United States Patent
Schuh et al.

(12)

(10) Patent No.: US 10,639,114 B2
(45) Date of Patent: May 5, 2020

(54) BIPOLAR MEDICAL INSTRUMENT

(71) Applicant: Auris Health, Inc., Redwood City, CA (US)

(72) Inventors: Travis Michael Schuh, Los Altos, CA (US); Erica Ding Chin, Redwood City, CA (US); Alex J. Niswander, Turtletown, TN (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/454,691

(22) Filed: Jun. 27, 2019

(65) Prior Publication Data

US 2020/0054405 A1 Feb. 20, 2020

Related U.S. Application Data

(60) Provisional application No. 62/719,437, filed on Aug. 17, 2018.

(51) Int. Cl.
| | |
|---|---|
| *A61B 18/14* | (2006.01) |
| *A61B 17/00* | (2006.01) |
| *A61B 34/35* | (2016.01) |
| *A61B 34/00* | (2016.01) |
| *A61B 18/12* | (2006.01) |

(Continued)

(52) U.S. Cl.
CPC .......... *A61B 34/35* (2016.02); *A61B 18/1206* (2013.01); *A61B 18/1445* (2013.01); *A61B 34/71* (2016.02); *A61B 2017/00017* (2013.01); *A61B 2017/00477* (2013.01); *A61B 2018/00577* (2013.01); *A61B 2018/00595* (2013.01); *A61B 2018/00601* (2013.01); *A61B 2018/126* (2013.01); *A61B 2034/305* (2016.02)

(58) Field of Classification Search
CPC combination set(s) only.
See application file for complete search history.

(56) References Cited

U.S. PATENT DOCUMENTS

| | | |
|---|---|---|
| 3,763,860 A | 10/1973 | Clarke |
| 4,040,413 A | 8/1977 | Ohshiro |
| 4,198,960 A | 4/1980 | Utsugi |

(Continued)

FOREIGN PATENT DOCUMENTS

| | | |
|---|---|---|
| EP | 1 321 106 | 6/2003 |
| EP | 1 849 423 | 10/2007 |

(Continued)

OTHER PUBLICATIONS

International Search Report and Written Opinion dated Sep. 9, 2019 in application No. PCT/US19/039416.

*Primary Examiner* — Michael F Peffley
*Assistant Examiner* — Amanda L Zink
(74) *Attorney, Agent, or Firm* — Knobbe, Martens, Olson & Bear, LLP

(57) ABSTRACT

Certain aspects relate to systems and techniques for a bipolar medical instrument. In one aspect, the medical instrument includes a first end effector, a first set of one or more distal pulleys coupled to the first end effector, and a wrist configured to house the first set of distal pulleys. The medical instrument also includes a plurality of cables extending through the wrist and a first insulating member formed between the first end effector and the first set of one or more distal pulleys.

19 Claims, 33 Drawing Sheets

(51) Int. Cl.
 A61B 34/30 (2016.01)
 A61B 18/00 (2006.01)

(56) References Cited

U.S. PATENT DOCUMENTS

| | | | |
|---|---|---|---|
| 4,470,407 A | 9/1984 | Hussein | |
| 4,532,935 A | 8/1985 | Wang et al. | |
| 4,685,458 A | 8/1987 | Leckrone | |
| 4,747,405 A | 5/1988 | Leckrone | |
| 4,898,574 A | 2/1990 | Uchiyama et al. | |
| 4,983,165 A | 1/1991 | Loiterman | |
| 5,029,574 A | 7/1991 | Shimamura et al. | |
| 5,085,659 A | 2/1992 | Rydell | |
| 5,196,023 A | 3/1993 | Martin | |
| 5,217,465 A | 6/1993 | Steppe | |
| 5,308,323 A | 5/1994 | Sogawa et al. | |
| 5,318,589 A | 6/1994 | Lichtman | |
| 5,325,848 A | 7/1994 | Adams et al. | |
| 5,342,381 A | 8/1994 | Tidemand | |
| 5,344,395 A | 9/1994 | Whalen et al. | |
| 5,353,783 A | 10/1994 | Nakao et al. | |
| 5,370,609 A | 12/1994 | Drasler et al. | |
| 5,372,124 A | 12/1994 | Takayama et al. | |
| 5,411,016 A | 5/1995 | Kume | |
| 5,431,649 A | 7/1995 | Mulier et al. | |
| 5,441,485 A | 8/1995 | Peters | |
| 5,449,356 A | 9/1995 | Walbrink | |
| 5,450,843 A | 9/1995 | Moll et al. | |
| 5,472,426 A | 12/1995 | Bonati et al. | |
| 5,496,267 A | 3/1996 | Drasler | |
| 5,501,667 A | 3/1996 | Verduin, Jr. | |
| 5,520,684 A | 5/1996 | Imran | |
| 5,545,170 A | 8/1996 | Hart | |
| 5,562,648 A | 10/1996 | Peterson | |
| 5,562,678 A | 10/1996 | Booker | |
| 5,572,999 A | 11/1996 | Funda et al. | |
| 5,573,535 A | 11/1996 | Viklund | |
| 5,613,973 A | 3/1997 | Jackson et al. | |
| 5,645,083 A | 7/1997 | Essig et al. | |
| 5,653,374 A | 8/1997 | Young et al. | |
| 5,658,311 A | 8/1997 | Baden | |
| 5,695,500 A | 12/1997 | Taylor et al. | |
| 5,697,949 A | 12/1997 | Giurtino et al. | |
| 5,710,870 A | 1/1998 | Ohm | |
| 5,716,325 A | 2/1998 | Bonutti | |
| 5,788,667 A | 8/1998 | Stoller | |
| 5,792,165 A * | 8/1998 | Klieman | A61B 17/29 606/170 |
| 5,797,900 A | 8/1998 | Madhani | |
| 5,810,770 A | 9/1998 | Chin et al. | |
| 5,893,869 A | 4/1999 | Barnhart | |
| 5,924,175 A | 7/1999 | Lippitt | |
| 5,989,230 A | 11/1999 | Frassica | |
| 6,071,281 A | 6/2000 | Burnside et al. | |
| 6,093,157 A | 7/2000 | Chandrasekaran | |
| 6,120,476 A | 9/2000 | Fung et al. | |
| 6,120,498 A | 9/2000 | Jani et al. | |
| 6,156,030 A | 12/2000 | Neev | |
| 6,174,318 B1 | 1/2001 | Bates et al. | |
| 6,206,903 B1 | 3/2001 | Ramans | |
| 6,183,435 B1 | 6/2001 | Bumbalough et al. | |
| 6,322,557 B1 | 11/2001 | Nikolaevich | |
| 6,375,635 B1 | 4/2002 | Moutafis | |
| 6,394,998 B1 | 5/2002 | Wallace et al. | |
| 6,405,078 B1 | 6/2002 | Moaddeb et al. | |
| 6,440,061 B1 | 8/2002 | Wenner et al. | |
| 6,508,823 B1 | 1/2003 | Gonon | |
| 6,522,906 B1 | 2/2003 | Salisbury et al. | |
| 6,577,891 B1 | 6/2003 | Jaross et al. | |
| 6,676,668 B2 | 1/2004 | Mercereau et al. | |
| 6,685,698 B2 | 2/2004 | Morley et al. | |
| 6,706,050 B1 | 3/2004 | Giannadakis | |
| 7,282,055 B2 | 10/2007 | Tsuruta | |
| 7,559,934 B2 | 7/2009 | Teague et al. | |
| 7,736,356 B2 | 6/2010 | Cooper et al. | |
| 7,963,911 B2 | 6/2011 | Turliuc | |
| 8,002,713 B2 | 8/2011 | Heske | |
| 8,038,598 B2 | 10/2011 | Khachi | |
| 8,092,397 B2 | 1/2012 | Wallace et al. | |
| 8,187,173 B2 | 5/2012 | Miyoshi | |
| 8,257,303 B2 | 9/2012 | Moll et al. | |
| 8,523,762 B2 | 9/2013 | Miyamoto et al. | |
| 8,540,748 B2 | 9/2013 | Murphy et al. | |
| 8,820,603 B2 | 9/2014 | Shelton et al. | |
| 8,882,660 B2 | 11/2014 | Phee et al. | |
| 8,945,163 B2 | 2/2015 | Voegele et al. | |
| 8,956,280 B2 | 2/2015 | Eversull et al. | |
| 9,345,456 B2 | 5/2016 | Tsonton et al. | |
| 9,460,536 B2 | 10/2016 | Hasegawa et al. | |
| 9,504,604 B2 | 11/2016 | Alvarez | |
| 9,561,083 B2 | 2/2017 | Yu et al. | |
| 9,592,042 B2 | 3/2017 | Titus | |
| 9,597,152 B2 | 3/2017 | Schaeffer | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,730,757 B2 | 8/2017 | Brudniok | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,350,390 B2 | 7/2019 | Moll et al. | |
| 10,482,599 B2 | 11/2019 | Mintz et al. | |
| 2002/0019644 A1 | 2/2002 | Hastings | |
| 2002/0111608 A1 | 8/2002 | Baerveldt | |
| 2002/0111621 A1 | 8/2002 | Wallace et al. | |
| 2003/0004455 A1 | 1/2003 | Kadziauskas | |
| 2003/0040681 A1 | 2/2003 | Ng et al. | |
| 2003/0065358 A1 | 4/2003 | Frecker | |
| 2003/0109877 A1 | 6/2003 | Morley | |
| 2003/0109889 A1 | 6/2003 | Mercereau | |
| 2003/0158545 A1 | 8/2003 | Hovda et al. | |
| 2003/0208189 A1 | 11/2003 | Payman | |
| 2004/0143253 A1 | 7/2004 | Vanney | |
| 2004/0153093 A1 | 8/2004 | Donovan | |
| 2004/0158261 A1 | 8/2004 | Vu | |
| 2004/0186349 A1 | 9/2004 | Ewers | |
| 2004/0193146 A1 | 9/2004 | Lee et al. | |
| 2004/0210116 A1 | 10/2004 | Nakao | |
| 2005/0033270 A1 | 2/2005 | Ramans et al. | |
| 2005/0054900 A1 | 3/2005 | Mawn | |
| 2005/0159645 A1 | 7/2005 | Bertolero | |
| 2005/0240178 A1 | 10/2005 | Morley et al. | |
| 2005/0261705 A1 | 11/2005 | Gist | |
| 2006/0015133 A1 | 1/2006 | Grayzel | |
| 2006/0058813 A1 | 3/2006 | Teague | |
| 2006/0116693 A1 | 6/2006 | Weisenburgh | |

(56) References Cited

U.S. PATENT DOCUMENTS

| | | |
|---|---|---|
| 2006/0135963 A1 | 6/2006 | Kick |
| 2006/0156875 A1 | 7/2006 | McRury et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135803 A1 | 6/2007 | Belson |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0046122 A1 | 2/2008 | Manzo et al. |
| 2008/0065111 A1 | 3/2008 | Blumenkranz |
| 2008/0125698 A1 | 5/2008 | Gerg et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2010/0004642 A1 | 1/2010 | Lumpkin |
| 2010/0010504 A1 | 1/2010 | Simaan et al. |
| 2010/0011901 A1 | 1/2010 | Burbank |
| 2010/0082017 A1 | 4/2010 | Zickler |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0226249 A1 | 9/2010 | Mohr |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0167611 A1 | 7/2011 | Williams |
| 2011/0213362 A1 | 9/2011 | Cunningham |
| 2011/0224660 A1 | 9/2011 | Neuberger et al. |
| 2011/0238064 A1* | 9/2011 | Williams ............ A61B 34/71 606/41 |
| 2011/0257641 A1 | 10/2011 | Hastings et al. |
| 2011/0276085 A1 | 11/2011 | Krzyzanowski |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0209315 A1 | 8/2012 | Amat |
| 2012/0232342 A1 | 9/2012 | Reydel |
| 2012/0253332 A1 | 10/2012 | Moll |
| 2012/0259320 A1 | 10/2012 | Loesel et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144274 A1 | 6/2013 | Stefanchik et al. |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0345686 A1 | 12/2013 | Brown |
| 2014/0005681 A1 | 1/2014 | Gee et al. |
| 2014/0039681 A1 | 2/2014 | Bowling |
| 2014/0046308 A1 | 2/2014 | Bischoff |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1 | 7/2014 | Ianchulev |
| 2014/0194905 A1 | 7/2014 | Kappel |
| 2014/0243849 A1 | 8/2014 | Saglam |
| 2014/0275956 A1 | 9/2014 | Fan |
| 2014/0276723 A1 | 9/2014 | Parihar |
| 2014/0276956 A1* | 9/2014 | Crainich ............ A61B 34/71 606/130 |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0127045 A1 | 5/2015 | Prestel |
| 2015/0164522 A1 | 6/2015 | Budiman |
| 2015/0164594 A1 | 6/2015 | Romo et al. |
| 2015/0164596 A1 | 6/2015 | Romo |
| 2015/0201917 A1 | 7/2015 | Snow |
| 2015/0202085 A1 | 7/2015 | Lemonis |
| 2015/0314110 A1 | 11/2015 | Park |
| 2015/0335480 A1 | 11/2015 | Alvarez et al. |
| 2016/0001038 A1 | 1/2016 | Romo et al. |
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0303743 A1 | 10/2016 | Rockrohr |
| 2016/0331358 A1 | 11/2016 | Gordon |
| 2016/0367324 A1 | 12/2016 | Sato et al. |
| 2017/0007337 A1 | 1/2017 | Dan |
| 2017/0049471 A1 | 2/2017 | Gaffney et al. |
| 2017/0065227 A1 | 3/2017 | Marrs |
| 2017/0095234 A1 | 4/2017 | Prisco et al. |
| 2017/0095295 A1 | 4/2017 | Overmyer |
| 2017/0100199 A1 | 4/2017 | Yu et al. |
| 2017/0119481 A1 | 5/2017 | Romo et al. |
| 2017/0135706 A1 | 5/2017 | Frey |
| 2017/0165011 A1 | 6/2017 | Bovay et al. |
| 2017/0172553 A1* | 6/2017 | Chaplin ............ A61B 17/2909 |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0319289 A1 | 11/2017 | Neff et al. |
| 2017/0333679 A1 | 11/2017 | Jiang |
| 2017/0340396 A1 | 11/2017 | Romo et al. |

(56) References Cited

U.S. PATENT DOCUMENTS

| | | |
|---|---|---|
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0177556 A1 | 6/2018 | Noonan et al. |
| 2018/0193049 A1 | 7/2018 | Heck et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0083183 A1 | 3/2019 | Moll et al. |
| 2019/0099231 A1 | 4/2019 | Bruehwiler |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0328213 A1 | 10/2019 | Landey et al. |
| 2019/0336238 A1 | 11/2019 | Yu |

FOREIGN PATENT DOCUMENTS

| | | |
|---|---|---|
| JP | 2005-270464 | 10/2005 |
| WO | WO 11/161218 | 12/2011 |
| WO | WO 13/107468 | 7/2013 |
| WO | WO 13/130895 | 9/2013 |
| WO | WO 17/114855 | 7/2017 |
| WO | WO 18/069679 | 4/2018 |

\* cited by examiner

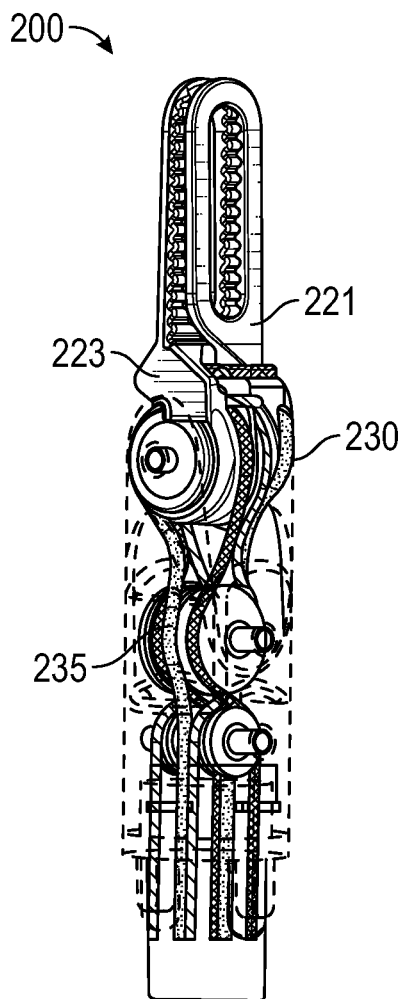
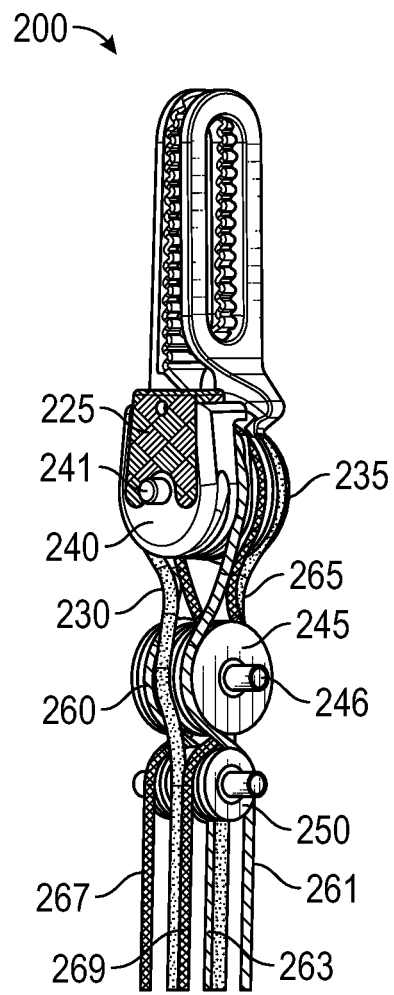
FIG. 21C
FIG. 21D

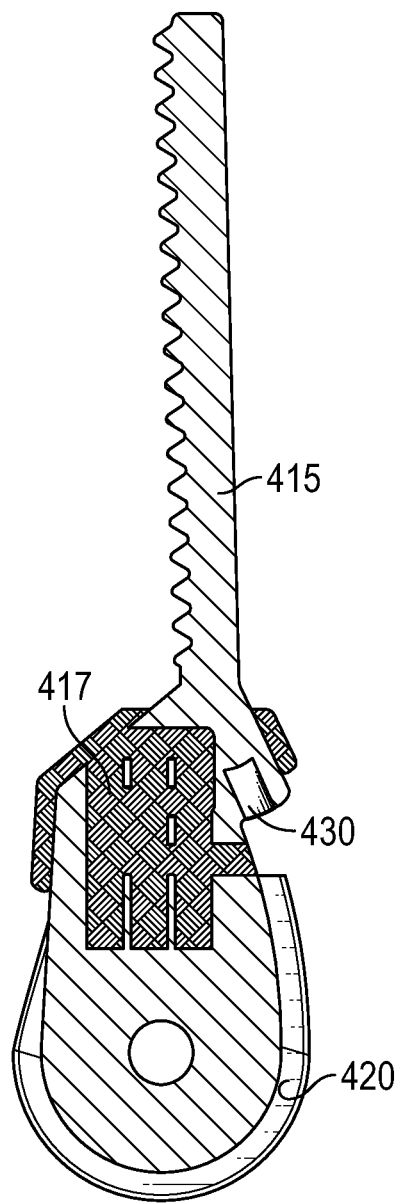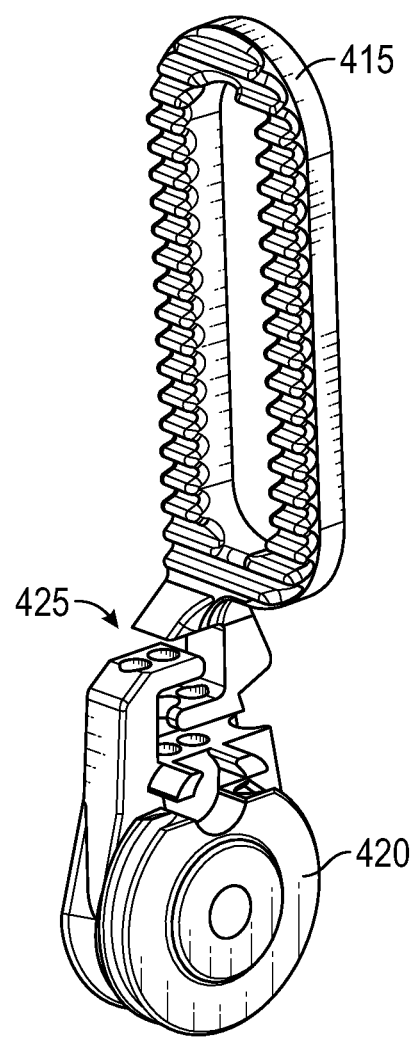
FIG. 26C
FIG. 26D

BIPOLAR MEDICAL INSTRUMENT

CROSS-REFERENCE TO RELATED APPLICATION(S)

This application claims the benefit of U.S. Provisional Application No. 62/719,437, filed Aug. 17, 2018, which is hereby incorporated by reference in its entirety.

TECHNICAL FIELD

The systems and methods disclosed herein are directed to a medical instrument, and more particularly to a medical instrument for cauterizing tissue.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotically-enabled medical system may be used to control the insertion and/or manipulation of the medical instrument and end effector, such as a medical instrument which can cauterize tissue. The robotically-enabled medical system may include a robotic arm or any other instrument positioning device. The robotically-enabled medical system may also include a controller used to control the positioning of the instrument during the procedure and control a current supplied to the end effector to control cauterization of tissue.

SUMMARY

The systems, methods and devices of this disclosure each have several innovative aspects, no single one of which is solely responsible for the desirable attributes disclosed herein.

In one aspect, there is provided a medical instrument comprising a first end effector; a first set of one or more distal pulleys coupled to the first end effector; a wrist configured to house the first set of distal pulleys; a plurality of cables extending through the wrist; and a first insulating member formed between the first end effector and the first set of one or more distal pulleys.

In another aspect, there is provided a medical instrument comprising a first end effector; a first set of one or more distal pulleys coupled to the first end effector; a wrist configured to house the first set of distal pulleys; a plurality of cables extending through the wrist; and a mechanical interlock including a pin formed between the first end effector and the first set of one or more distal pulleys.

In yet another aspect, there is provided a method of actuating end effectors in multiple degrees of movement, the method comprising advancing or retracting a first set of one or more cable segments engaged with a first distal pulley, the first distal pulley coupled to a first end effector and configured to actuate the first end effector in a first degree of movement, the first end effector electrically insulated from the first distal pulley via a first insulating member; and advancing or retracting a second set of one or more cable segments engaged with a second distal pulley, the second distal pulley coupled to a second end effector and configured to actuate the second end effector in a second degree of movement.

In still yet another aspect, there is provided a method comprising providing an instrument including: a first end effector, a first set of one or more distal pulleys coupled to the first end effector, a wrist configured to house the first set of distal pulleys, and a plurality of cables extending through the wrist; and molding a first insulating member between the first end effector and the first set of distal pulleys, wherein the first insulating member electrically isolates the first end effector from the first set of one or more distal pulleys.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 21A-21D illustrate a plurality of views of an embodiment of a bipolar medical instrument in accordance with aspects of this disclosure.

FIGS. 26A-26D illustrate a plurality of views of the end effector and distal pulley assembly of the instrument in FIG. 25.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
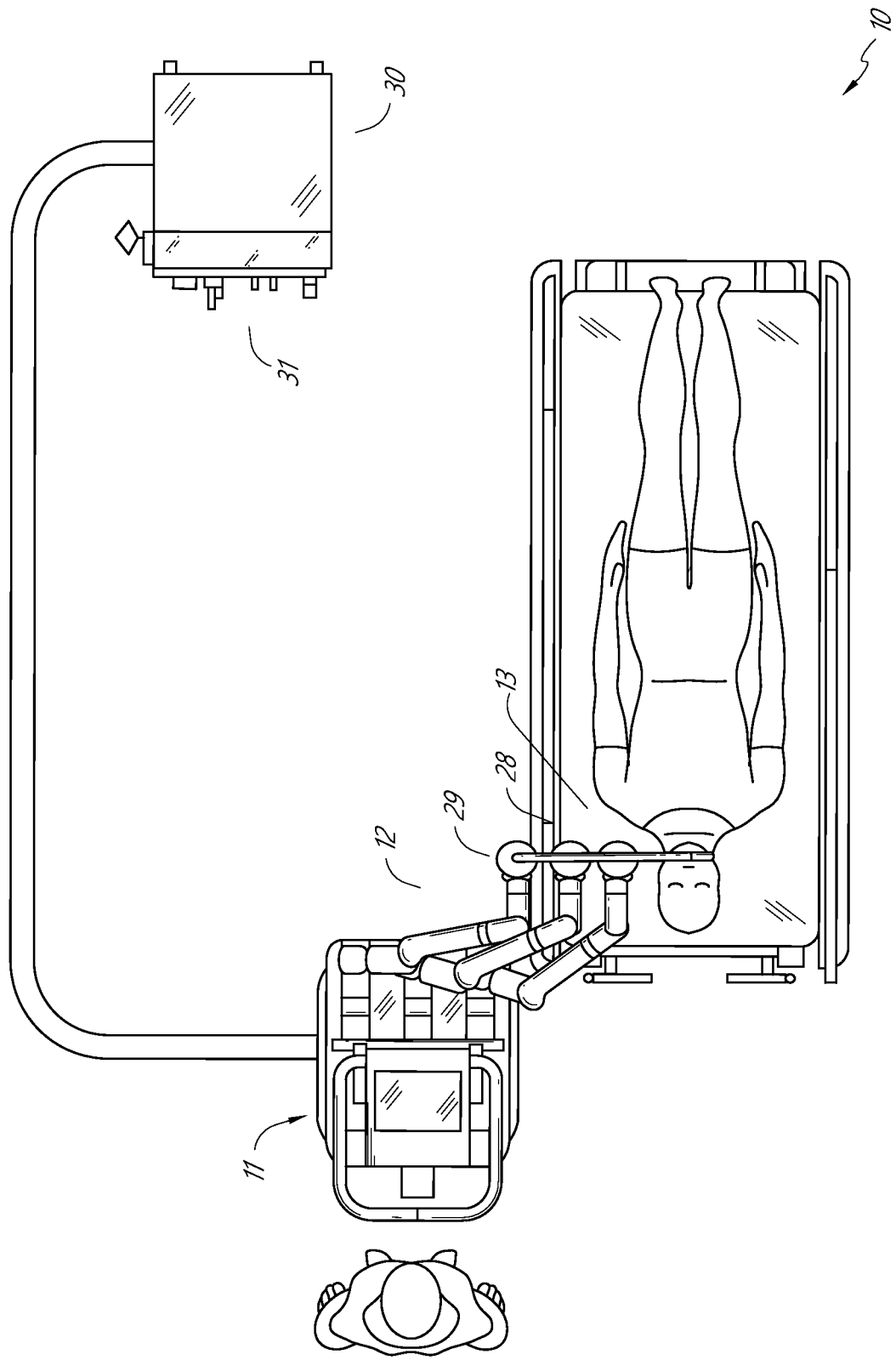
FIG. 1 illustrates an embodiment of a cart-based robotic system arranged for diagnostic and/or therapeutic bronchoscopy procedure(s).
Figure 2:
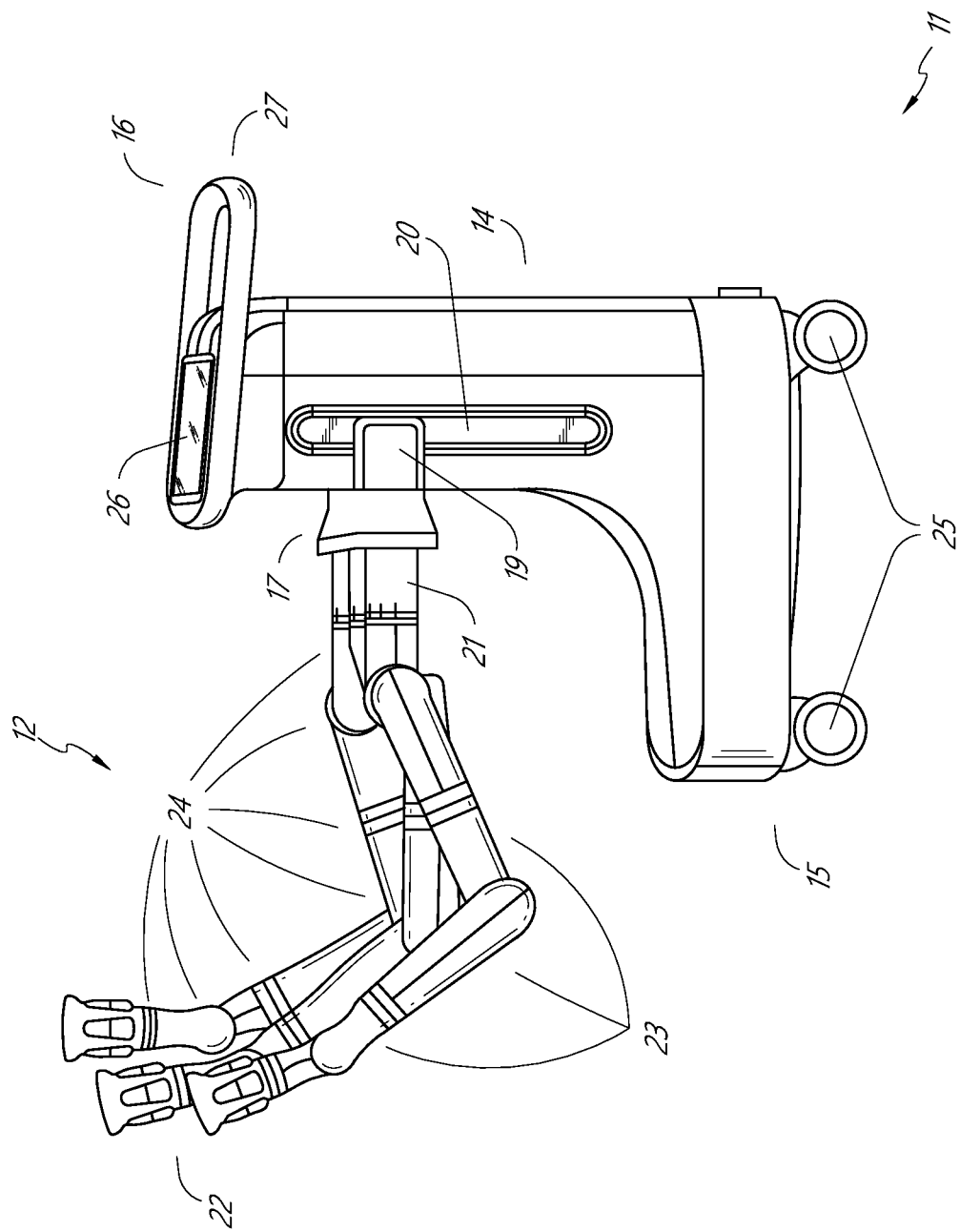
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver (also referred to as an instrument drive mechanism (IDM)) from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or repositioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
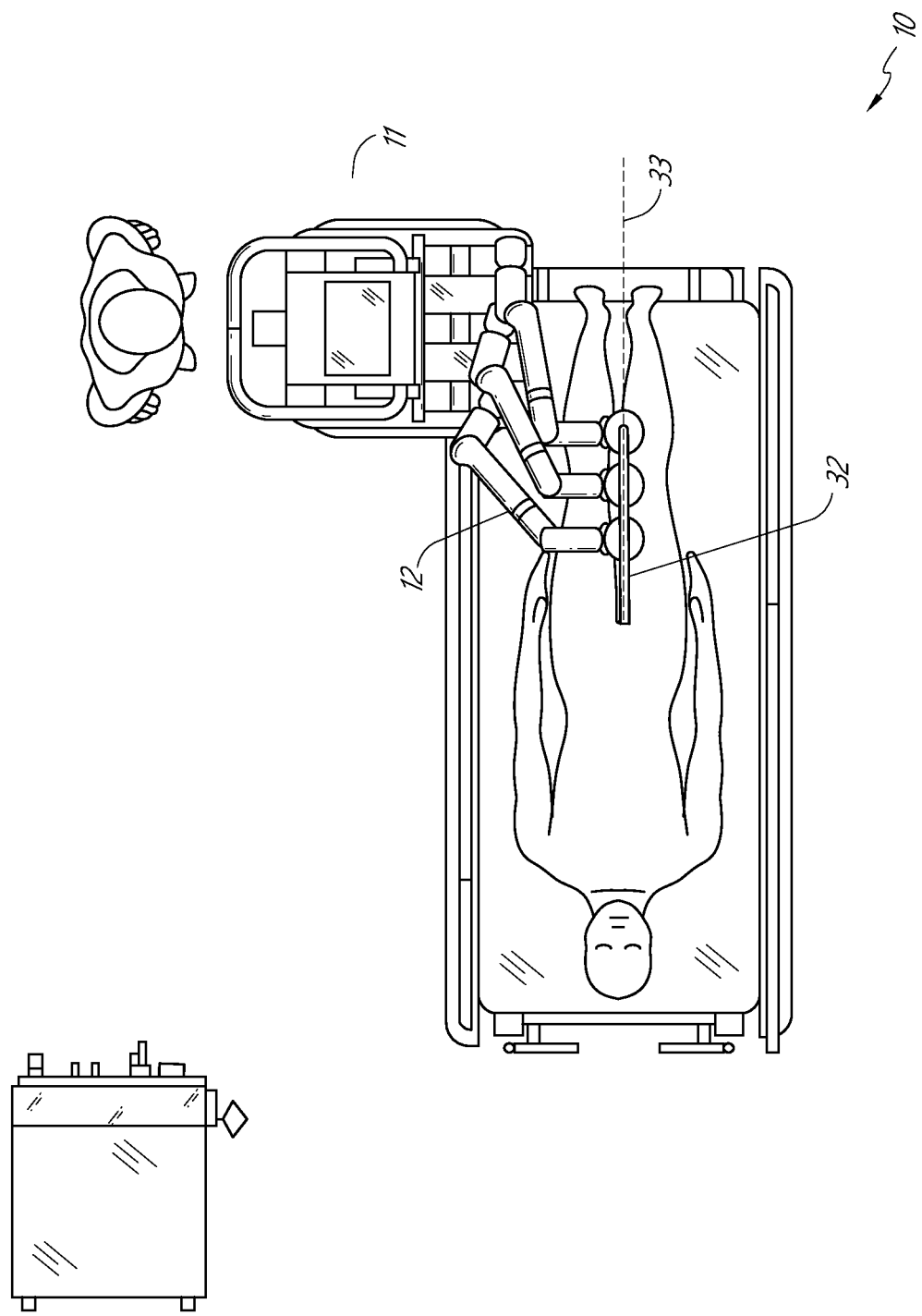
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
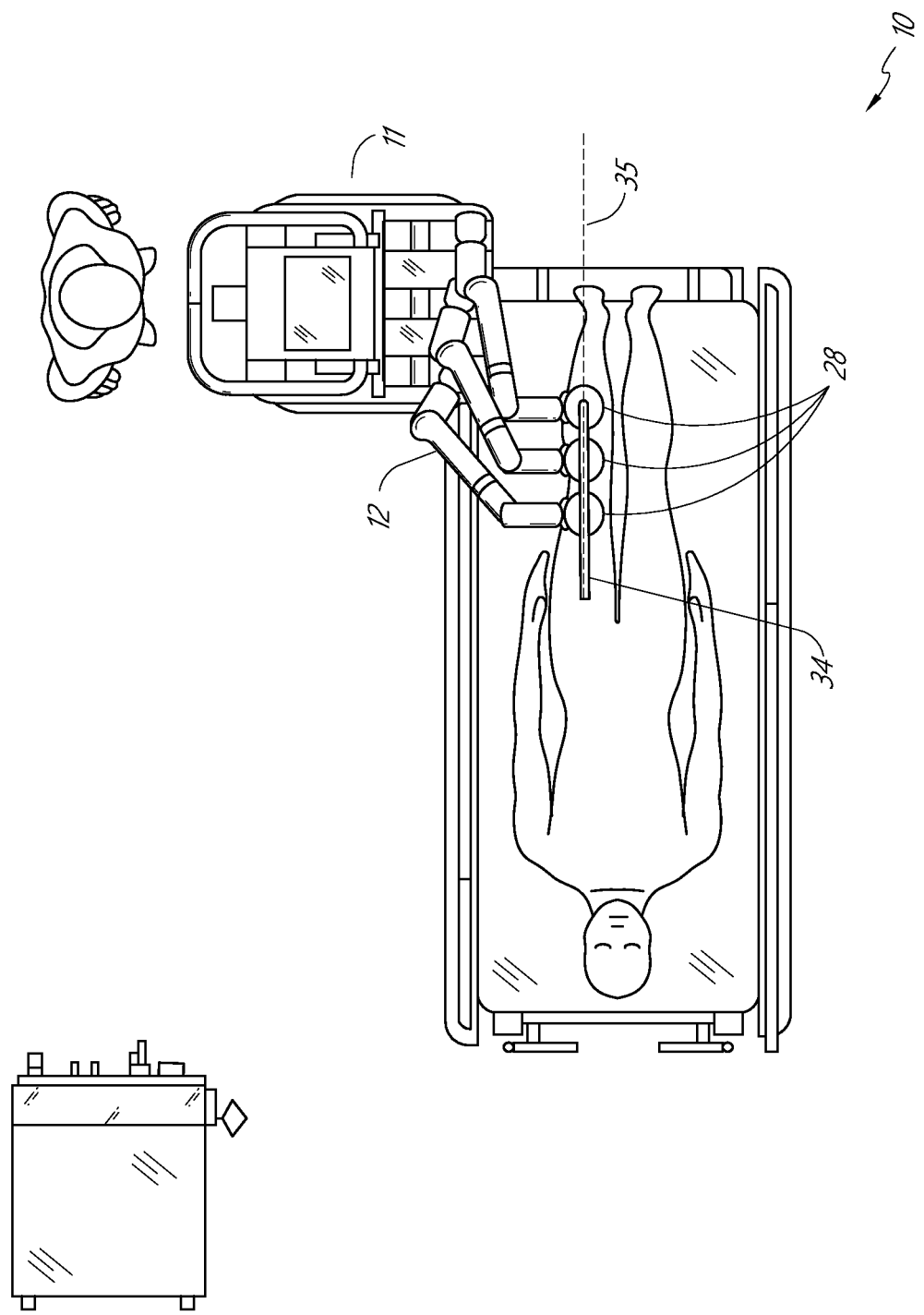
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
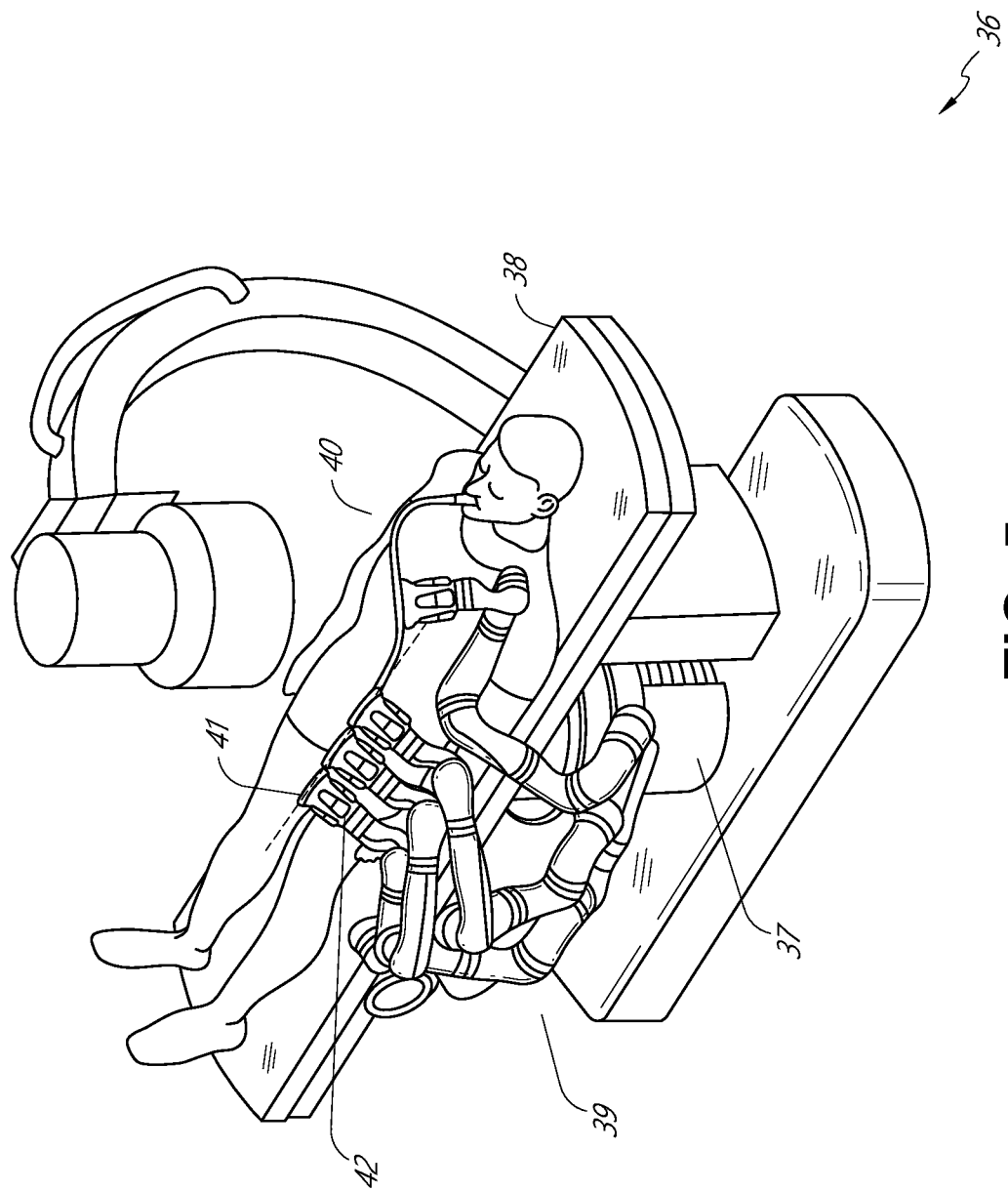
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
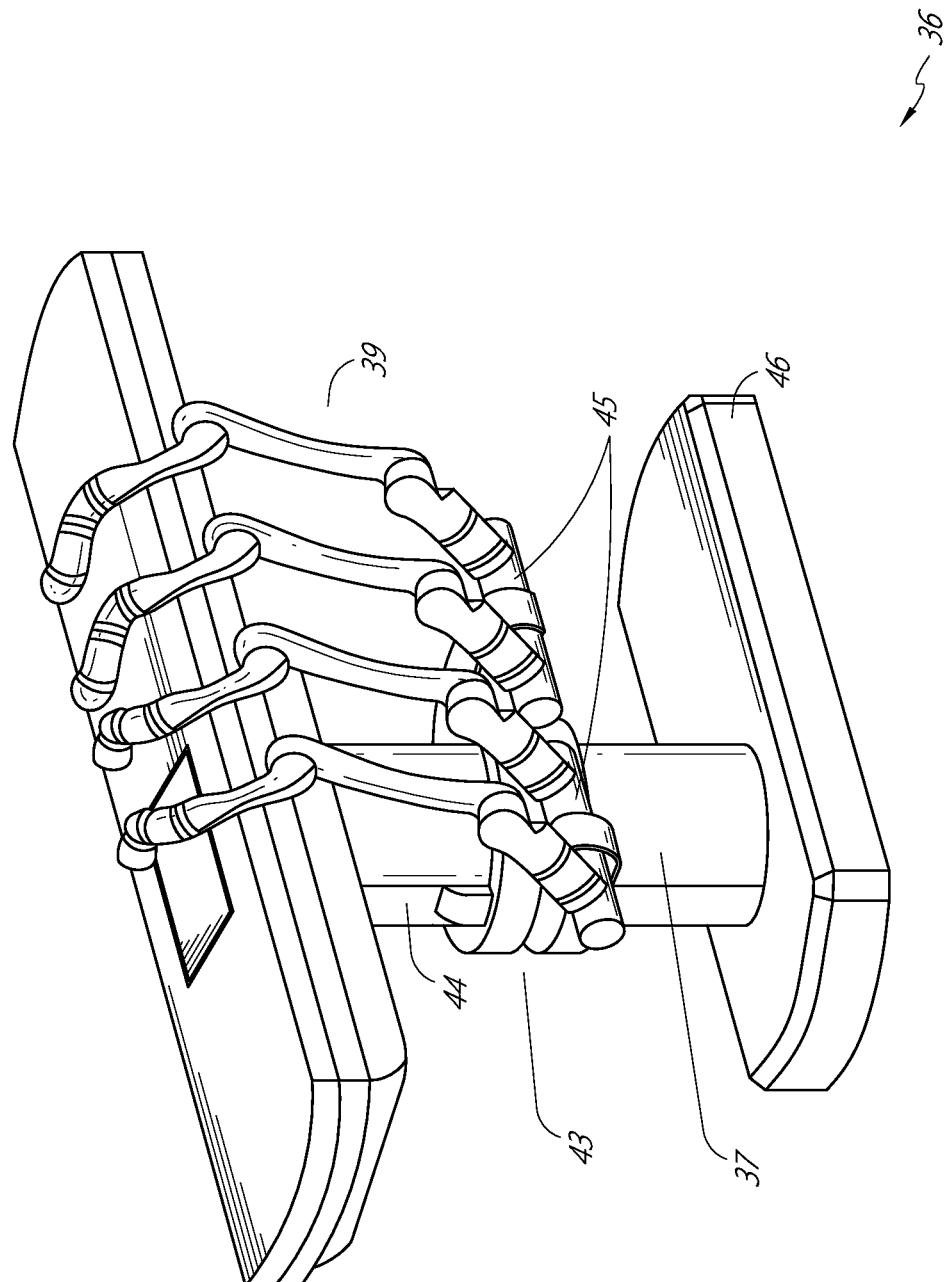
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
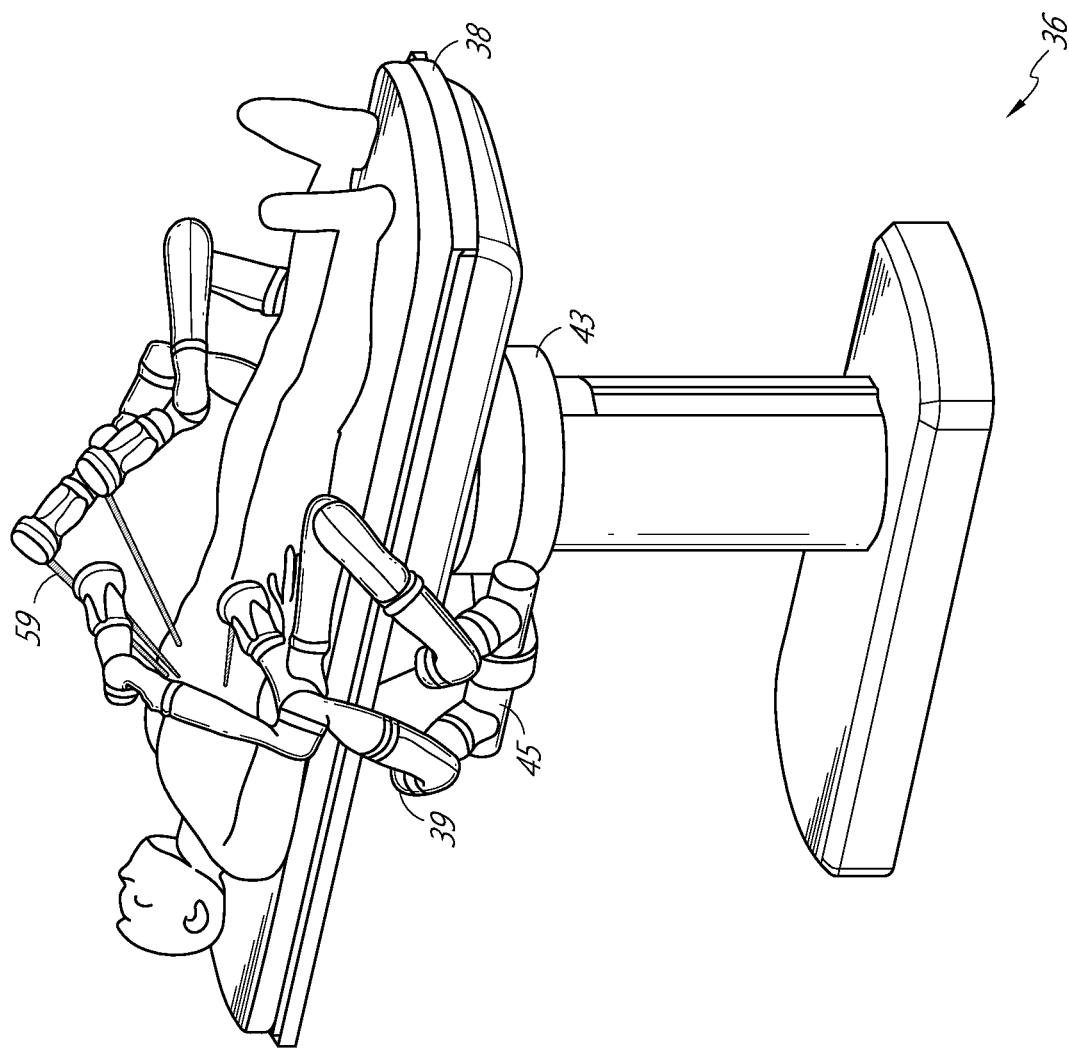
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
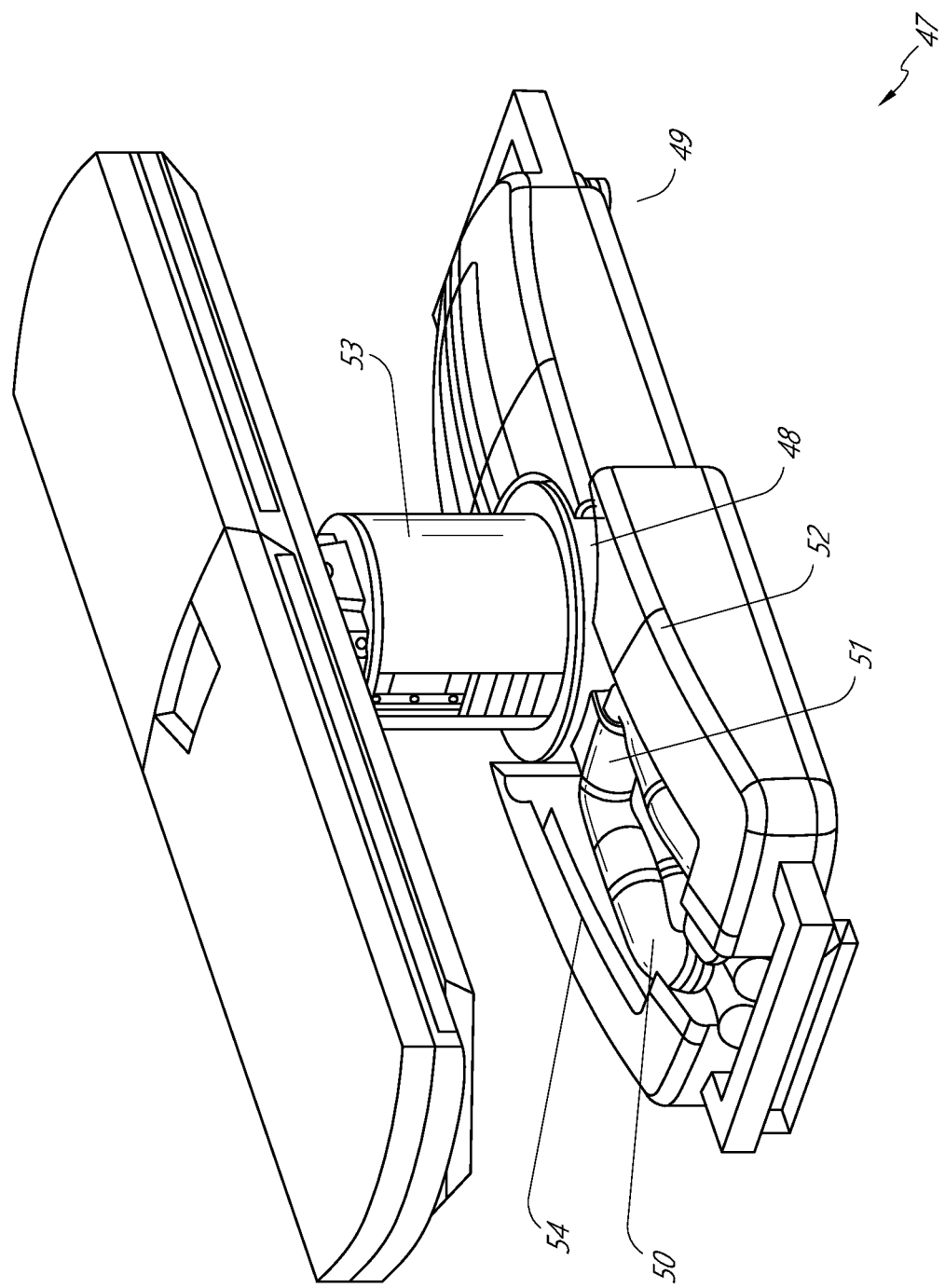
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
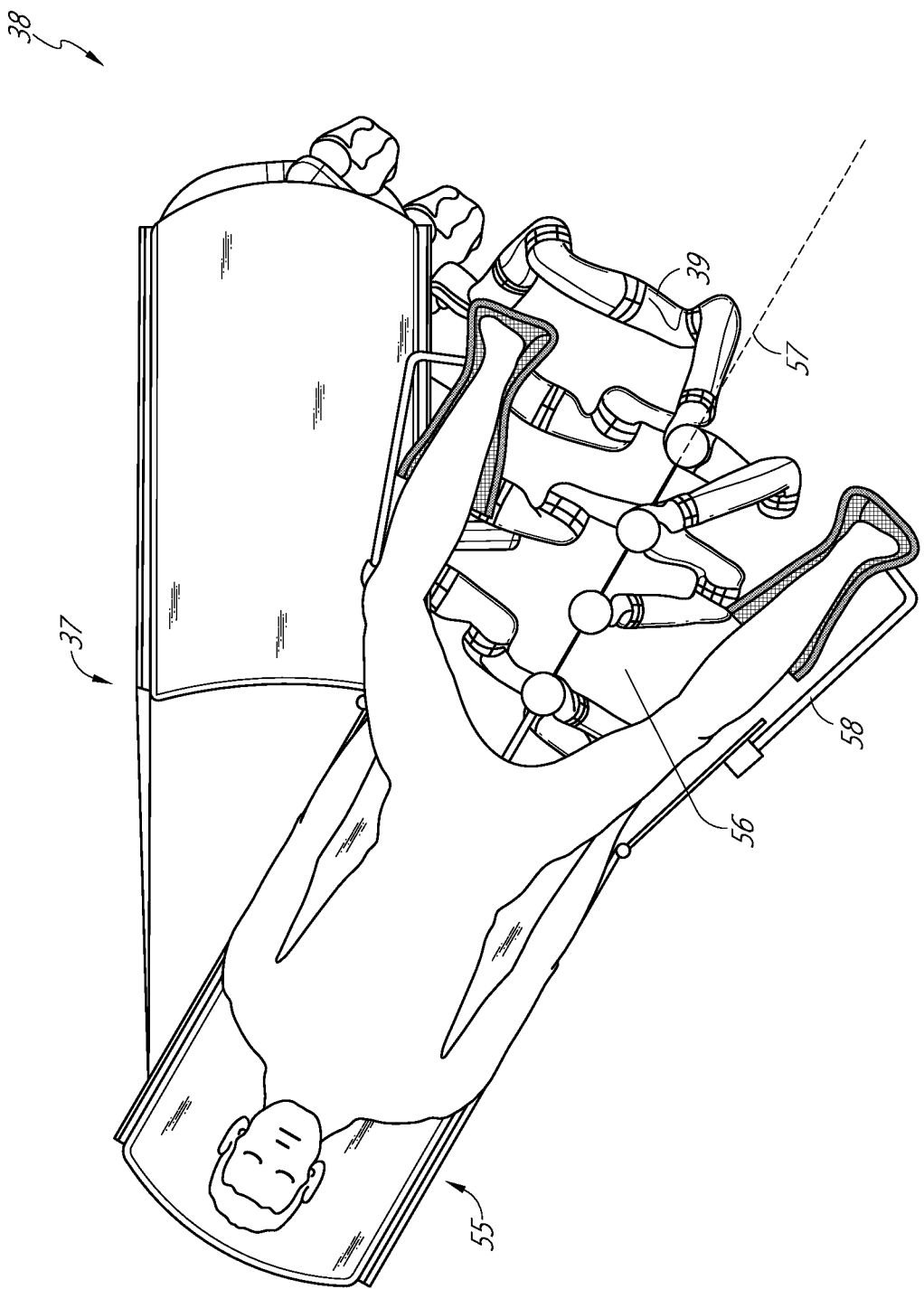
FIG. 8 illustrates an embodiment of a table-based robotic system configured for a ureteroscopy procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
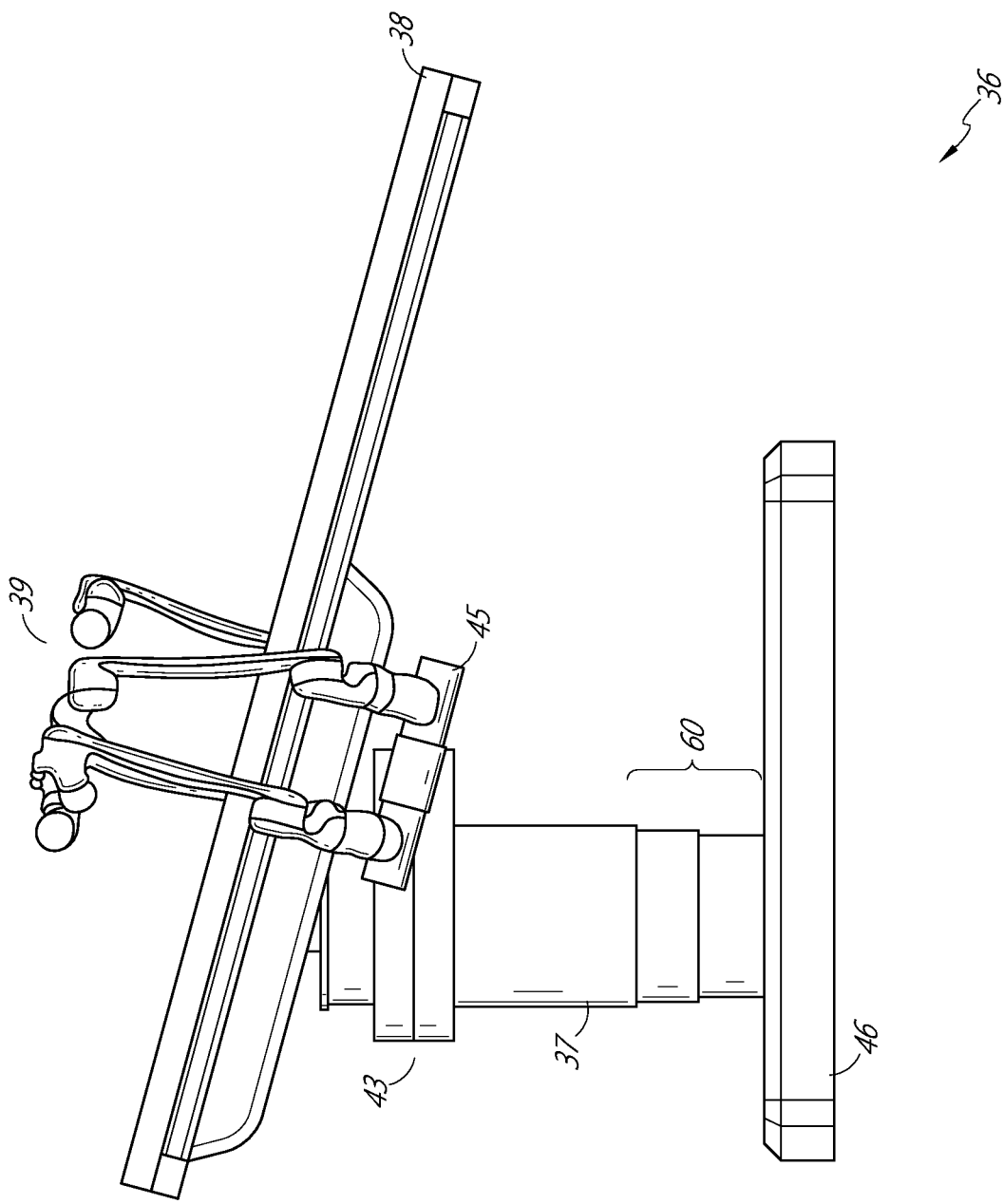
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
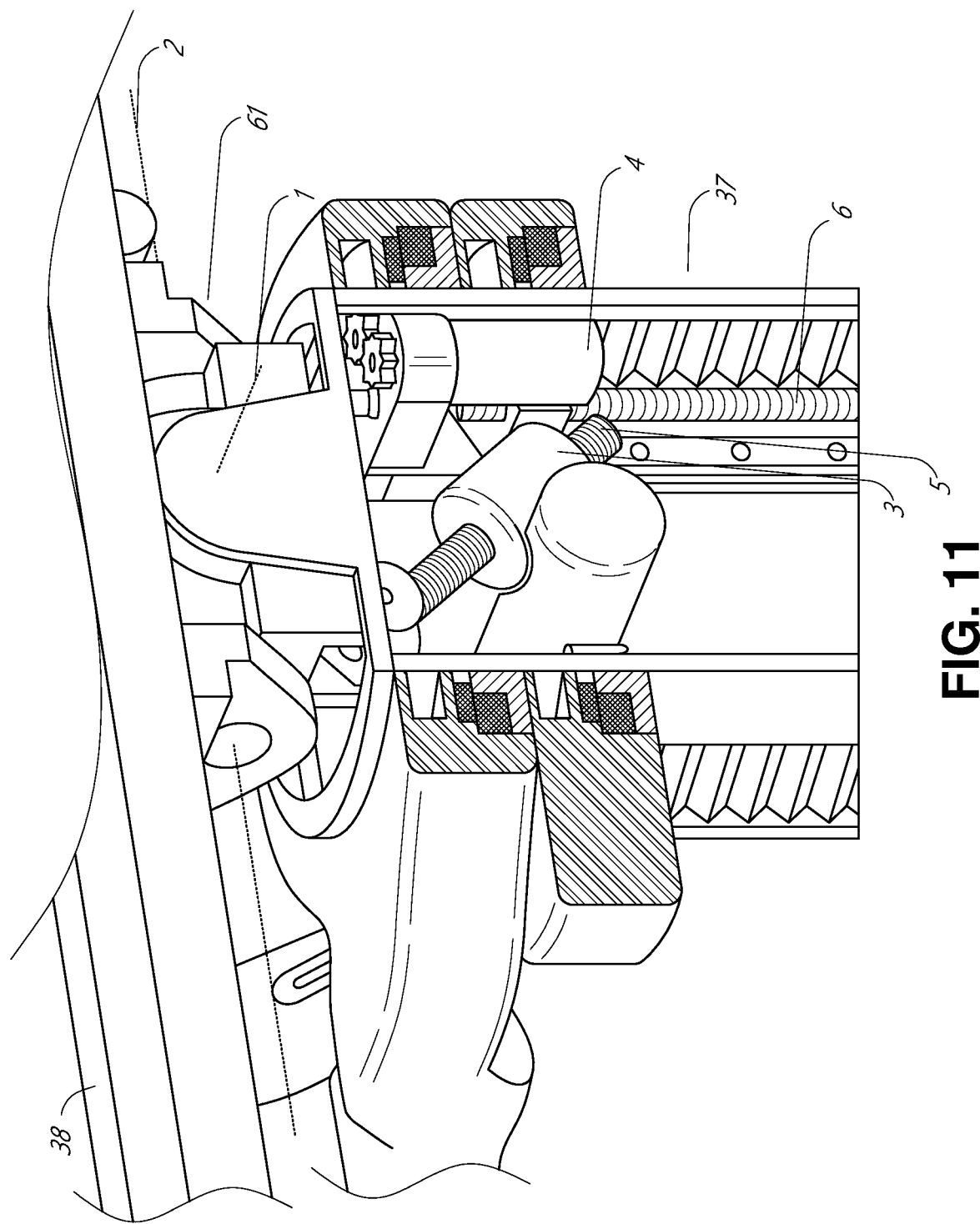
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
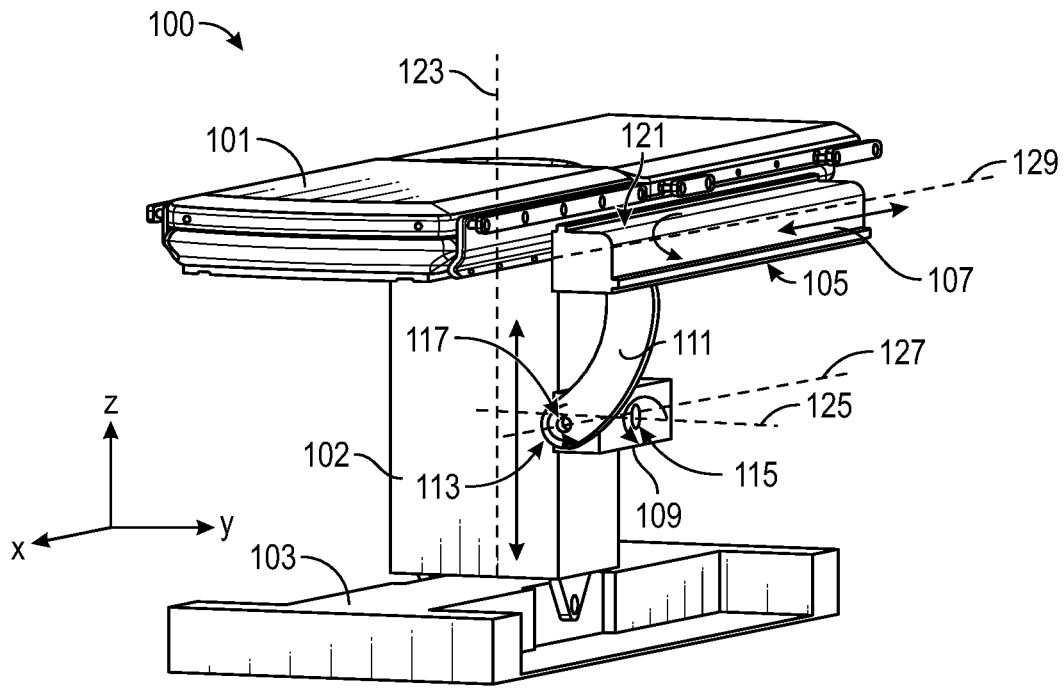
FIG. 12 illustrates an alternative embodiment of a table-based robotic system.
Figure 13:
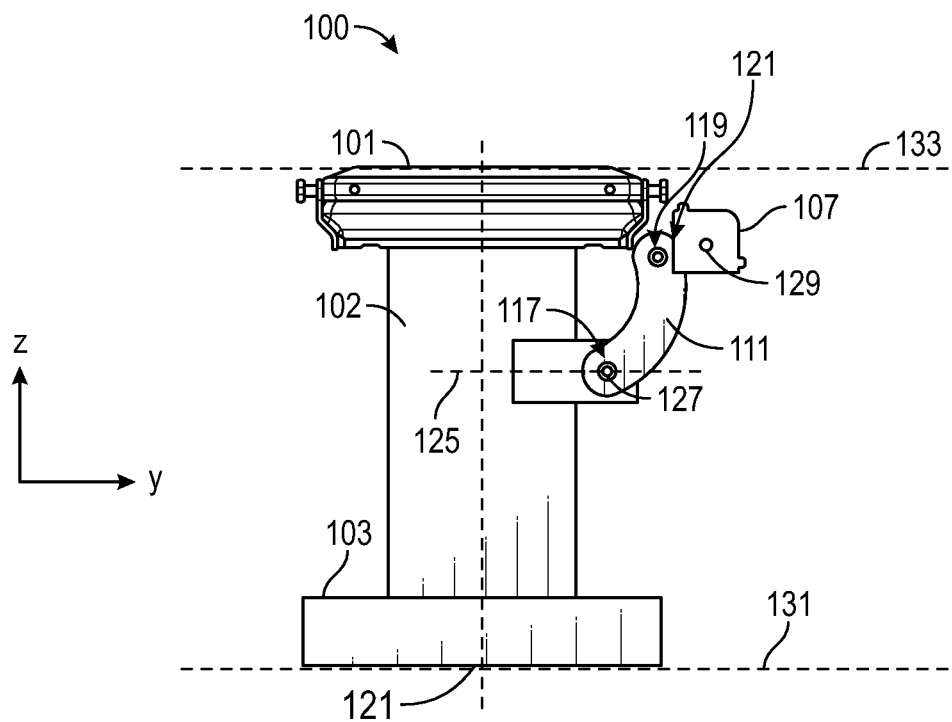
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
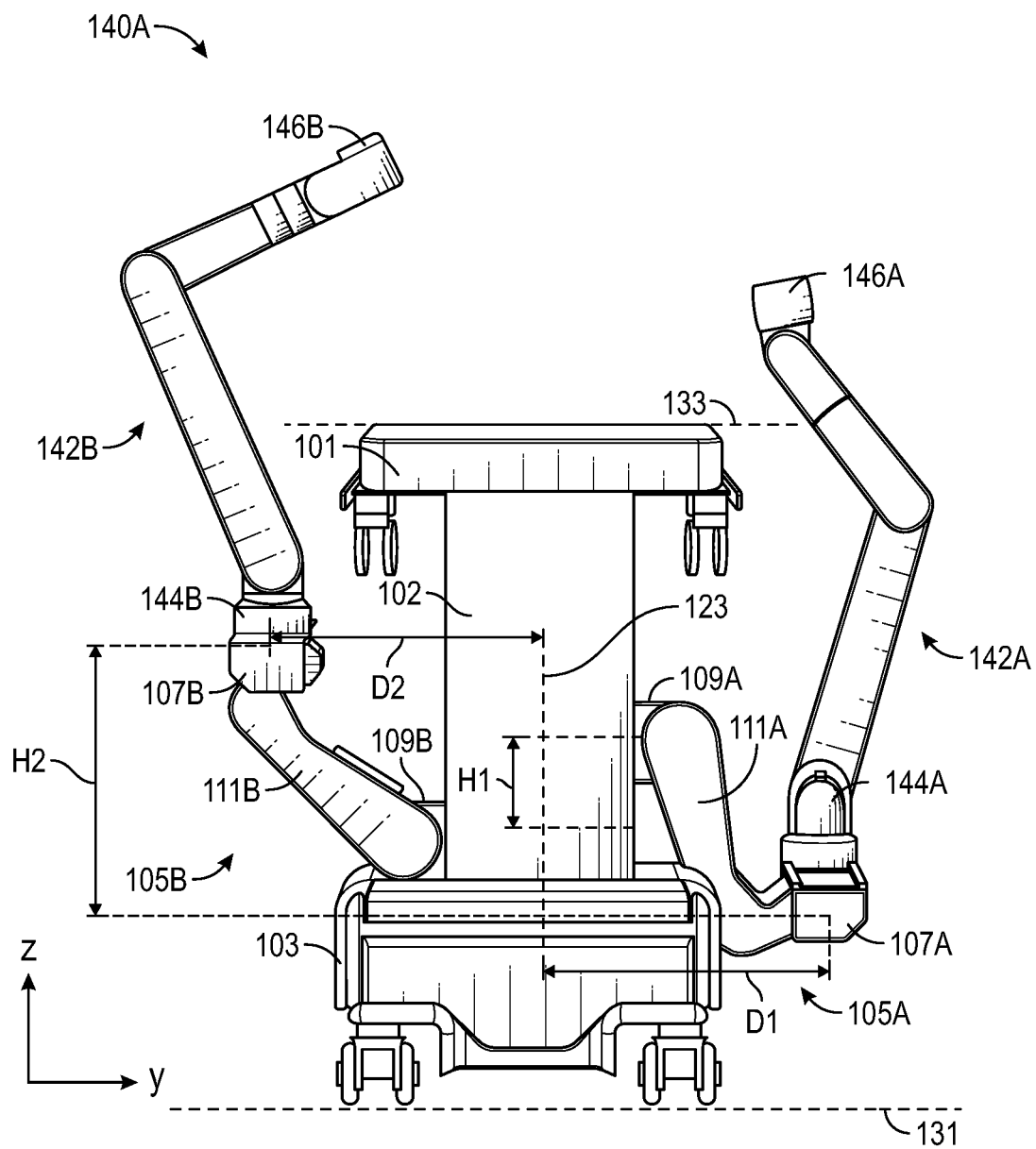
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
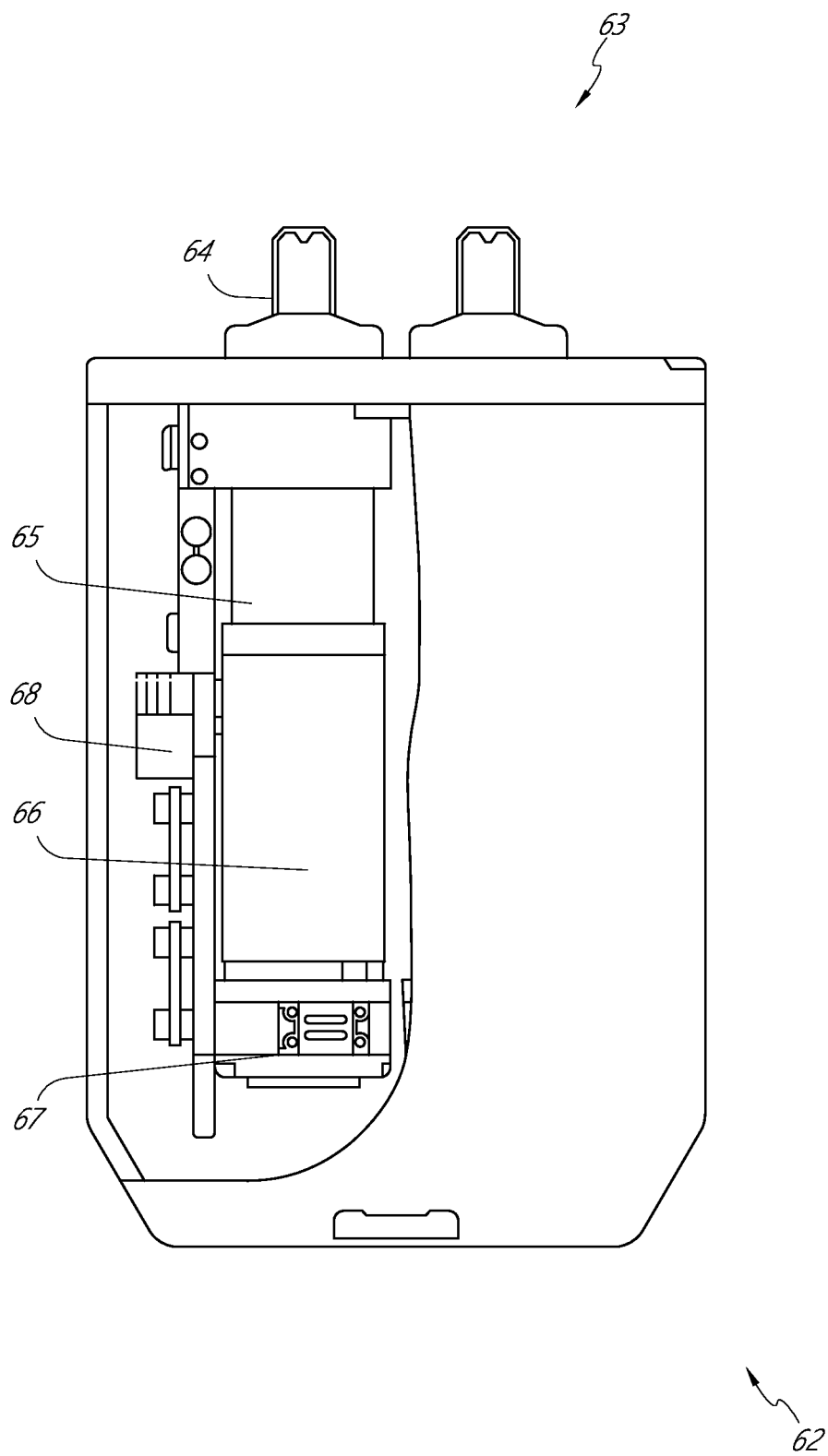
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
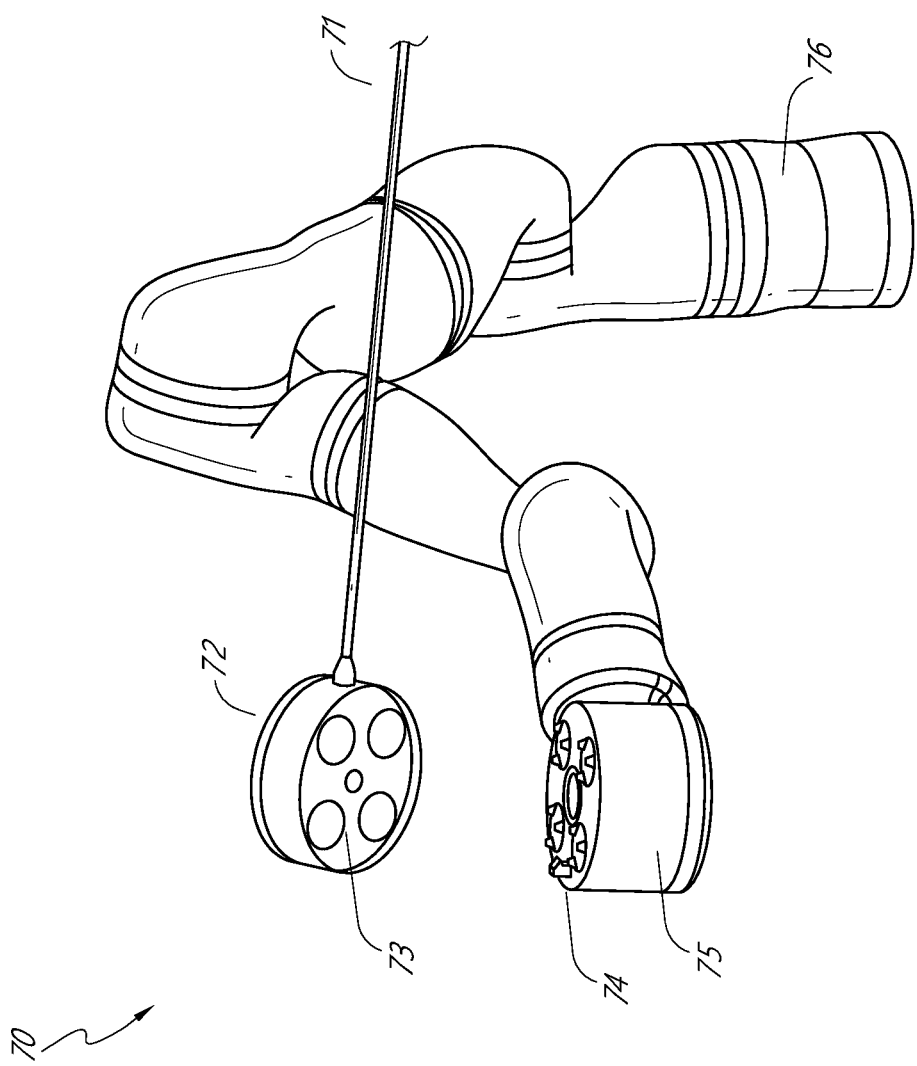
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
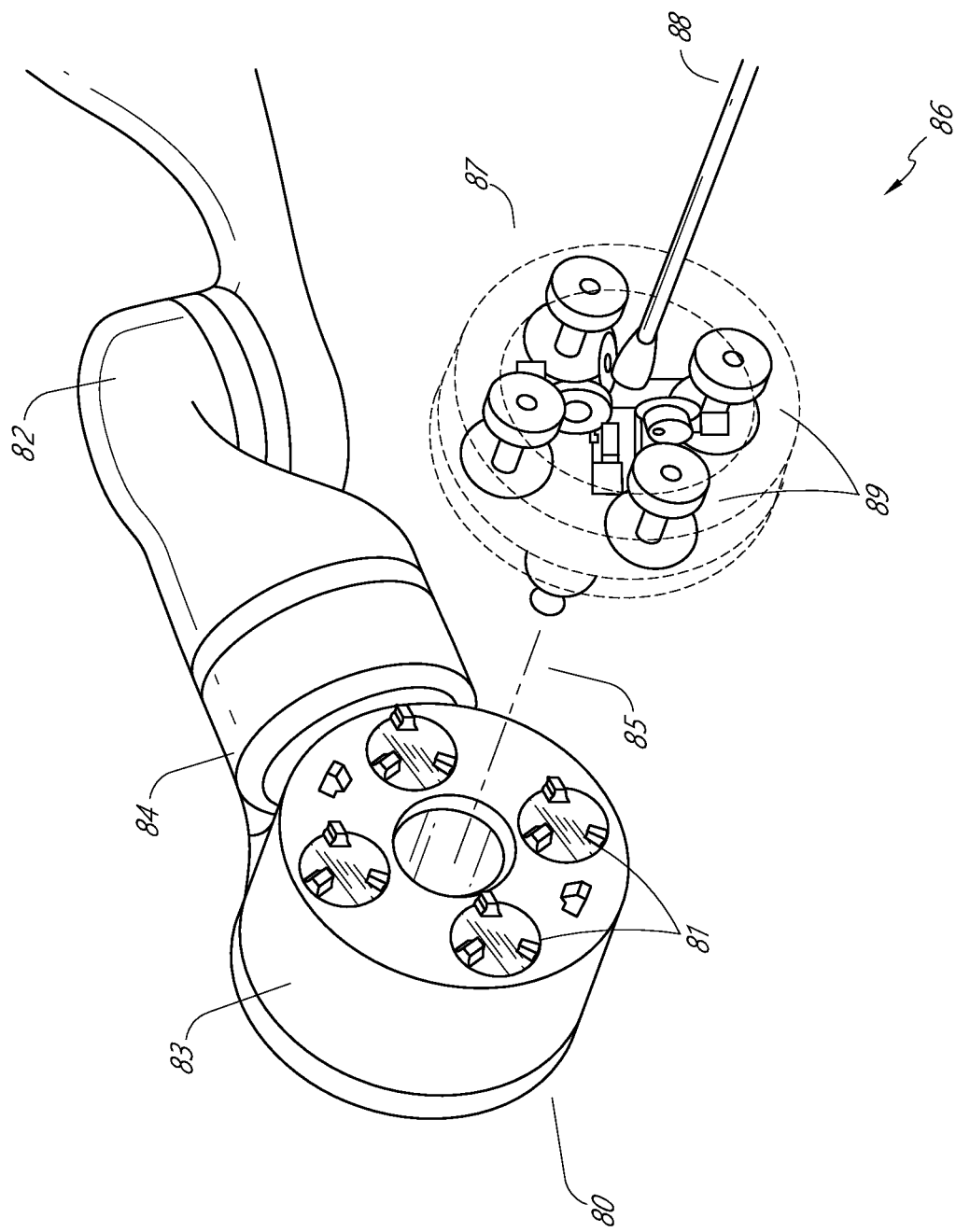
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
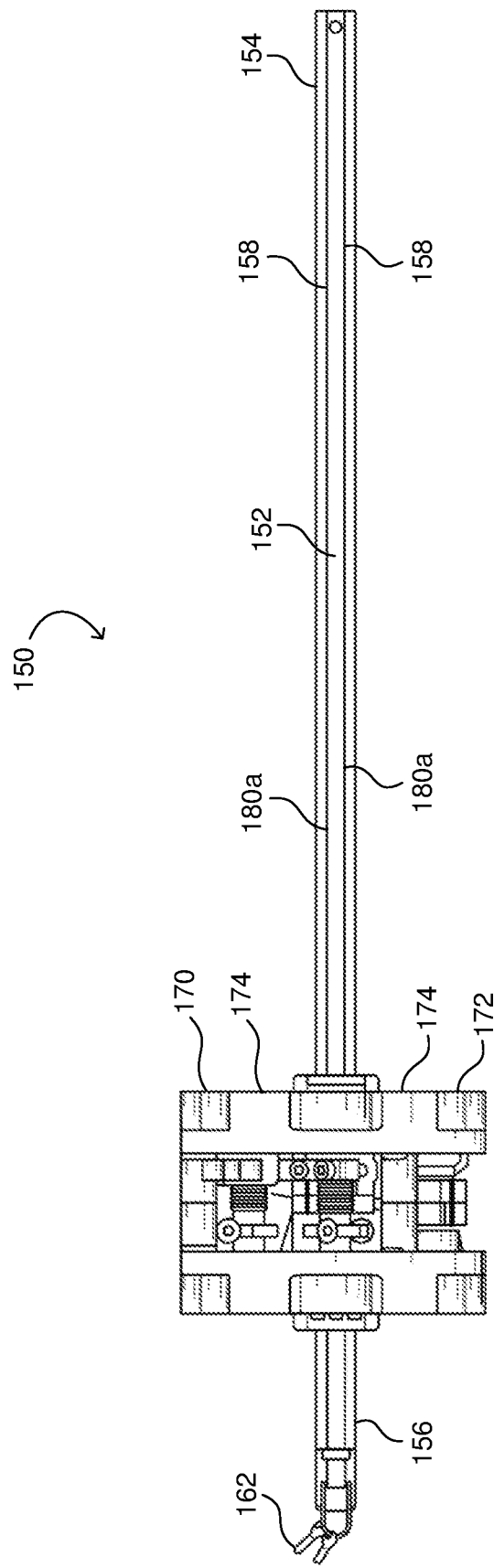
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
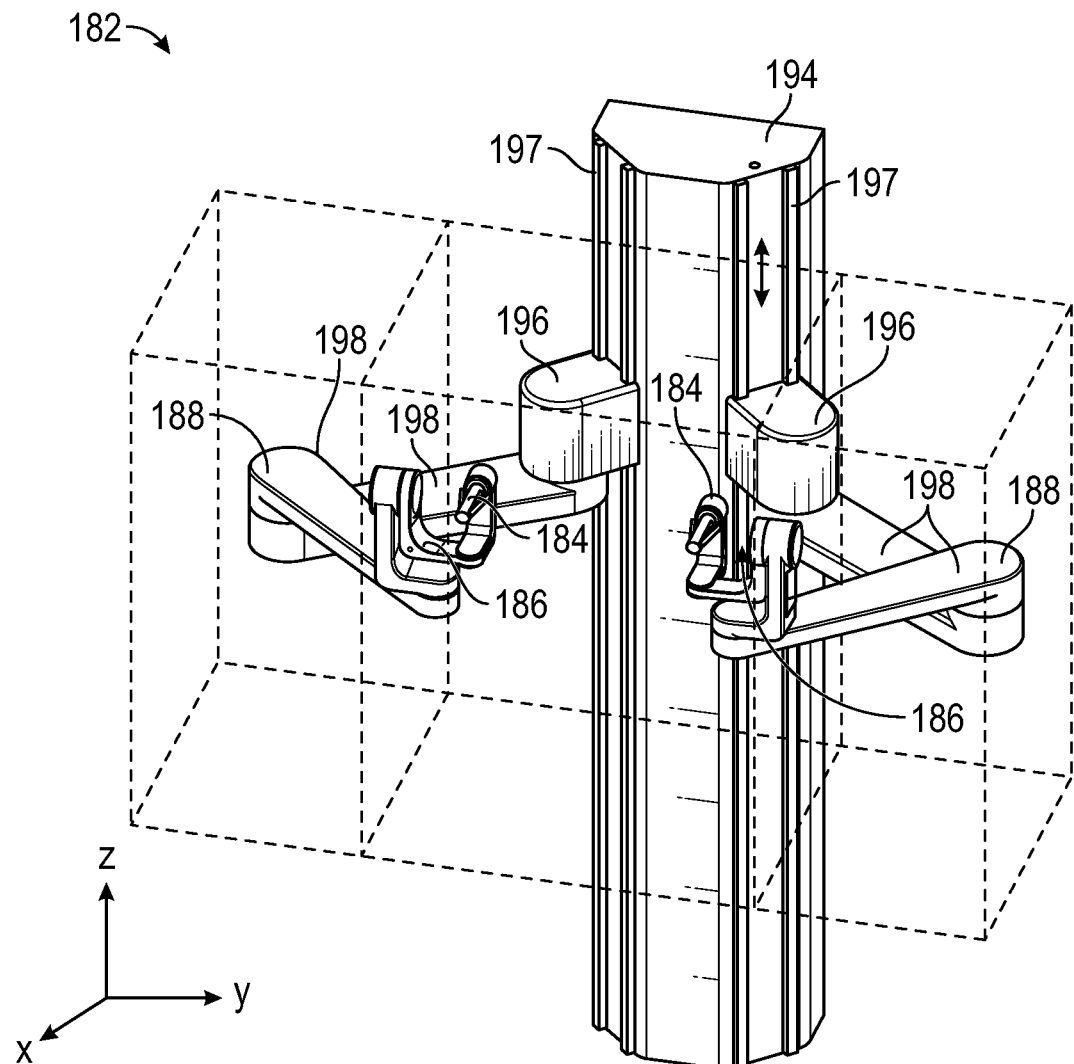
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
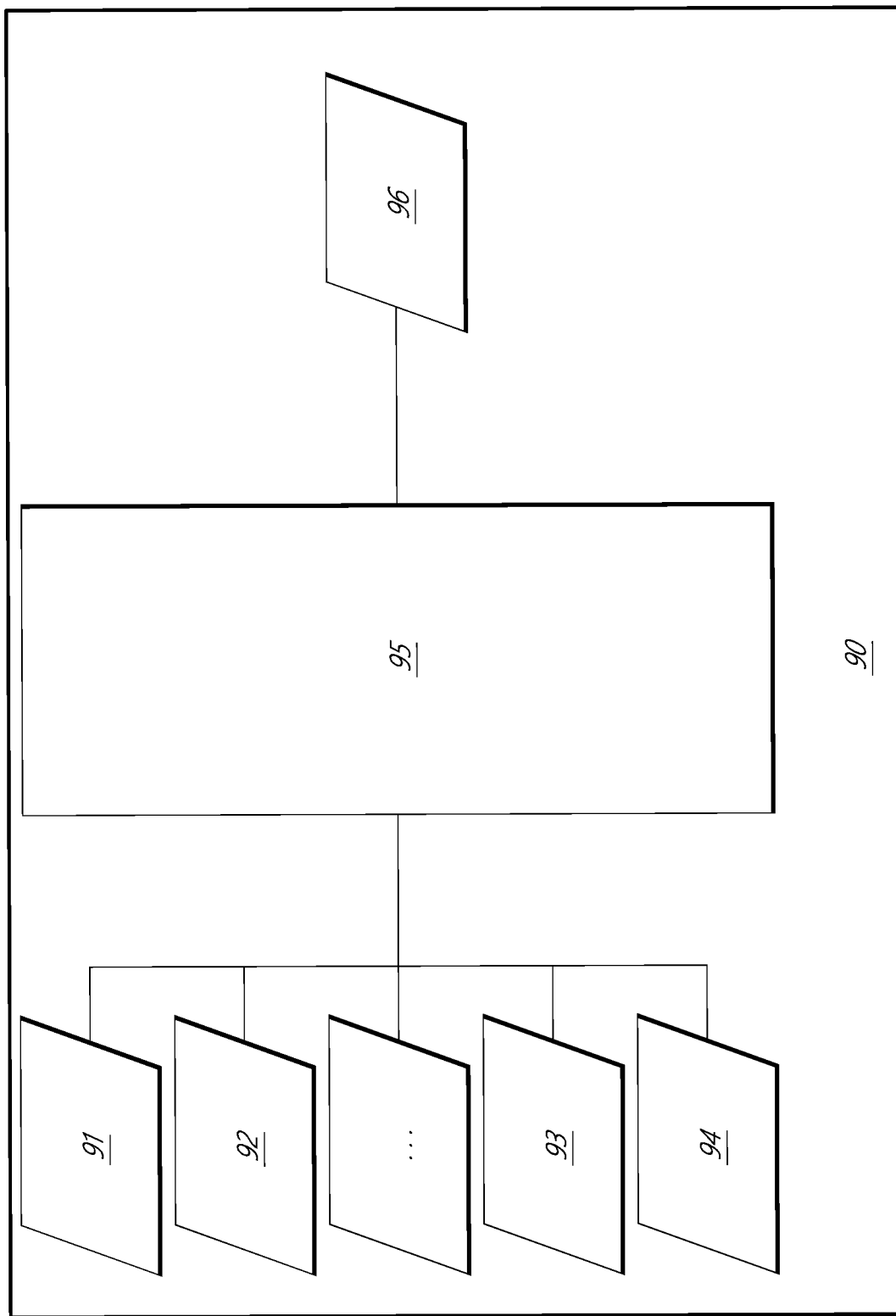
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Bipolar Medical Instruments

Embodiments of the disclosure relate to a bipolar medical instrument which can be used to cauterize tissue. The bipolar medical instrument can be attached to an IDM at a distal end or portion of a robotic arm such that the bipolar medical instrument can be controlled by a robotic system. A pair of end effectors located at the distal end of the bipolar medical instrument may be embodied as a pair of forceps or a grasper. The end effectors can cauterize (e.g., burn) or seal patient tissue positioned between them in a controlled manner by applying electrical energy to the end effectors (e.g., jaws of the grasper). For example, a voltage difference can be applied between a first end effector (e.g., a first jaw of a grasper) and a second end effector (e.g., a second jaw of the grasper), thereby causing current to flow from the first end effector to the second end effector. The heated area can therefore be confined to the patient's tissue in the region between the first and second end effectors (e.g., the first and second jaws of the grasper). The use of such a bipolar medical instrument for cauterization may facilitate better control of current and heat near the target area, resulting in fewer inadvertent patient burns.

The bipolar medical instrument may be electrically coupled to a generator (e.g., an electrosurgical unit (ESU)) configured to apply a voltage difference between two end effectors, thereby causing an electric current to flow between the end effectors. To ensure that the current flows between the end effectors, rather than through a short in another location within the bipolar medical instrument, the two electrical paths supplying the voltage difference to the end effectors are electrically isolated from each other. One technique for electrically isolating the end effects is to utilize distal pulleys that are formed of an electrically insulating material, which are mechanically fixed to the end effectors. However, due to the material properties of such electrically insulating material, the distal pulleys may occupy a larger area than distal pulleys formed of metal that provide similar functionality. As using distal pulleys formed of metal can reduce distal pulley size, the overall diameter of the bipolar medical instrument can be decreased, thereby allowing the distal pulleys to fit in a smaller diameter wrist (e.g., a 5-5.5 mm outer diameter wrist). By having a smaller diameter wrist, this can result in a smaller incision formed in a patient during surgery. Thus, aspects of this disclosure relate to systems and techniques for electrically isolating the electrical paths providing the voltage difference to the end effectors of a bipolar medical instrument, while maintaining an instrument of relatively small diameter.

A. Bipolar Medical Instruments Including a Single Isolated Grip

Figure 21A:
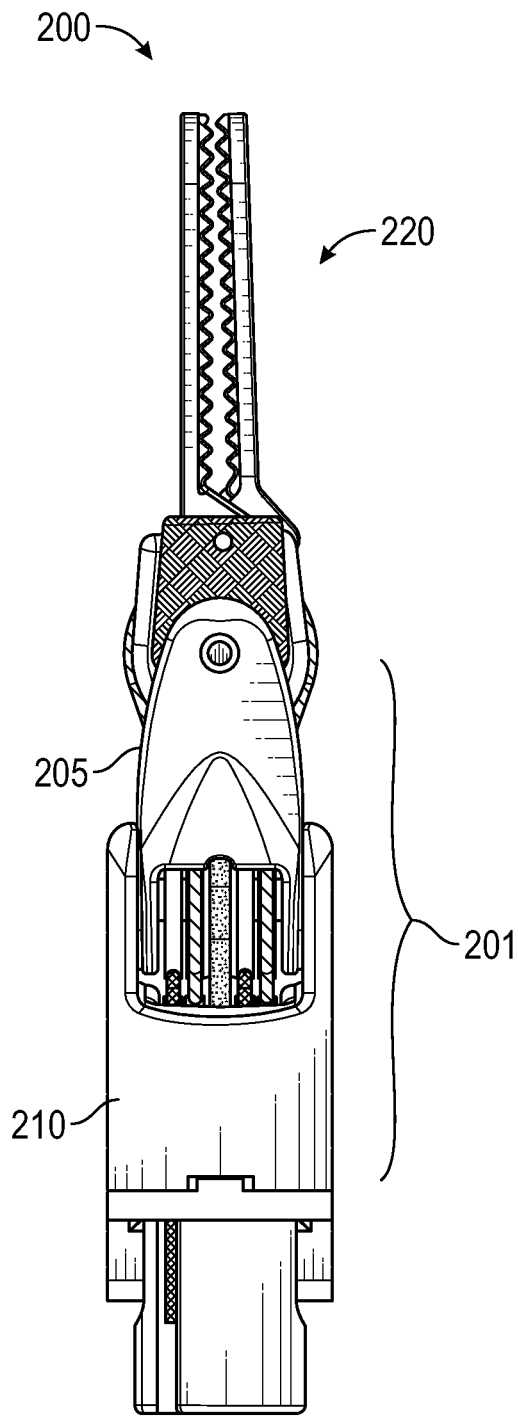
Figure 21B:
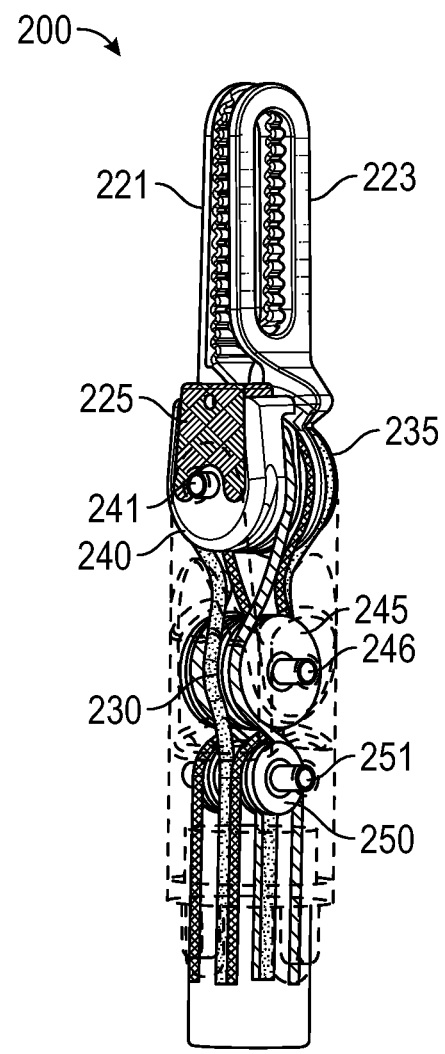

FIGS. 21A-21D illustrate a plurality of views of an embodiment of a bipolar medical instrument having a single isolated grip in accordance with aspects of this disclosure. In particular, FIG. 21A illustrates a view of the bipolar medical instrument 200 in which a wrist 201 is visible. FIGS. 21B and 21C illustrate additional views of the bipolar medical instrument 200 in which the wrist 201 is illustrated as transparent to provide a view of the internals of the wrist 201. FIG. 21D illustrates another view of the bipolar medical instrument 200 in which the wrist 201 is not shown to provide a view of cable paths within the wrist 201.

With reference to FIGS. 21A and 21B, the bipolar medical instrument 200 includes the wrist 201 and an end effector 220. The wrist 201 includes a distal clevis 205 and a proximal clevis 210. The end effector 220 may comprise a first end effector 221 and a second end effector 223. In some embodiments, the end effector 220 may be a grasping device, wherein the first end effector 221 may include a first jaw and the second end effector 223 may include a second jaw.

The bipolar medical instrument 200 may further include an insulating member (also referred to as an insulating skirt) 225, a first electrical cable 230, a second electrical cable 235, a set of one or more distal pulleys 240, a distal axle 241, a set of one or more proximal pulleys 245, a proximal axle 246, a set of one or more proximal redirect pulleys 250, and a proximal redirect axle 251. Further, as illustrated in FIG. 21D, the bipolar medical instrument 200 further includes a first drive cable 260 including two first cable segments 261 and 263, and a second drive cable 265 including two second cable segments 267 and 269.

Referring to the cable paths illustrated in FIG. 21D, the bipolar medical instrument 200 may be configured to be actuated in accordance with an N+1 actuation technique, where N is a number of degrees of freedom (DOF) in which the wrist 201 is configured to be actuated and N+1 is a number of cable segments configured to control actuation of the wrist 201. For example, the first end effector 221 may be actuated in a first DOF with respect to the distal axle 241 (e.g., defining a yaw axis) by the two first cable segments 261 and 263 (e.g., by advancing one of the first cable segments 261, 263 while retracting the other of the first cable segments 261, 263). Similarly, the second end effector 223 may be actuated in a second DOF with respect to the distal axle 241 by the two second cable segments 267 and 269 (e.g., by advancing one of the second cable segments 267, 269 while retracting the other of the second cable segments 267, 269). The distal clevis 205 may be actuated in a third DOF with respect to the proximal axle 246 (e.g., defining a pitch axis) by advancing both of the first cable segments 261 and 263 while retracting both of the second cable segments 267 and 269, or vice versa.

In the embodiment of FIGS. 21A-21D, since there are four cable segments 261, 263, 267, and 269 (e.g., N+1=4), the bipolar medical instrument 200 may be configured for actuation in three DOF (e.g., N=3). By coordinating the control of the actuation of both the first and second end effectors 221 and 223 (e.g., by a processor of the robotic system 10 of FIG. 1), the system may be able to provide three DOF control to a user, including yaw control (movement of both end effectors 221 and 223 in the same direction), pitch control (movement of the distal clevis 205), and grip control (contracting or separating the end effectors 221 and 223) of the bipolar medical instrument 200.

As shown in the cable path of FIG. 21D, in one embodiment, there may be pulleys that are not shared by the first cable segments 261 and 263 and the second cable segments 267 and 269 (e.g., each cable segment may be engaged with its own one of the proximal pulleys 245 and proximal redirect pulleys 250). However, the first electrical cable 230 and the second electrical cable 235 may share one of each of the proximal pulleys 245 and proximal redirect pulleys 250. For example, with respect to the shared proximal pulley 245, the first electrical cable 230 may run on one side of the shared proximal pulley 245 and the second electrical cable 235 may run on the other side of the shared proximal pulley 245.

The distal ends of the first and second end effectors 221 and 223 may have a plurality of teeth arranged facing each other in a complimentary fashion. However, this disclosure is not limited thereto, and in some embodiments, the distal ends of the first and second end effectors 221 and 223 may be smooth. In other embodiments, the distal ends of the first and second end effectors 221 and 223 can have other types of protrusions, including saw-tooth, ridges, or any other surface facing each other. As discussed above, the bipolar medical instrument 200 may be electrically coupled to a generator that is configured to apply a voltage difference between the first and second end effectors 221 and 223, thereby causing an electric current to flow between the first and second end effectors 221 and 223. Thus, the first and second end effectors 221 and 223 may be formed of electrically conductive material(s).

In the embodiment of FIGS. 21A-21D, the instrument comprises a single insulating member 225. The insulating member 225 is formed between the first end effector 221 and the distal pulley 240 and is configured to electrically insulate the first end effector 221 from the distal pulley 240. This is advantageous as both the first end effector 221 and the distal pulley 240 can be formed at least in part of a conductive material, such as a metal, which can provide other benefits such as space conservation and less wear. Thus, the first end effector 221 and the distal pulley 240 may be electrically decoupled from one another.

The insulating member 225 may be formed of an electrically insulating material, such as, for example a material with a high dielectric strength (e.g., urethane, peek, ultem, epoxy resin, ceramic, one or more plastics, etc.). The insulating member 225 may be molded between the first end effector 221 and the distal pulley 240. In some embodiments, the insulating member 225 may be injection molded into a pocket that is formed between the first end effector 221 and the distal pulley 240. The insulating member 225 may also be designed to occupy as much area within the distal clevis 205 as possible to prevent stray currents from flowing between the first end effector 221 and other electrically charged conductors within the wrist 201, thereby preventing inadvertently damaging tissue. In some embodiments, the insulating member 225 may occupy at least 25% of a surface defined by the outer face of the insulating member 225 and the distal pulley 240. In other embodiments, the insulating member 225 may occupy 40% or more of the outer face of the insulating member 225 and the distal pulley 240.

Figure 23:
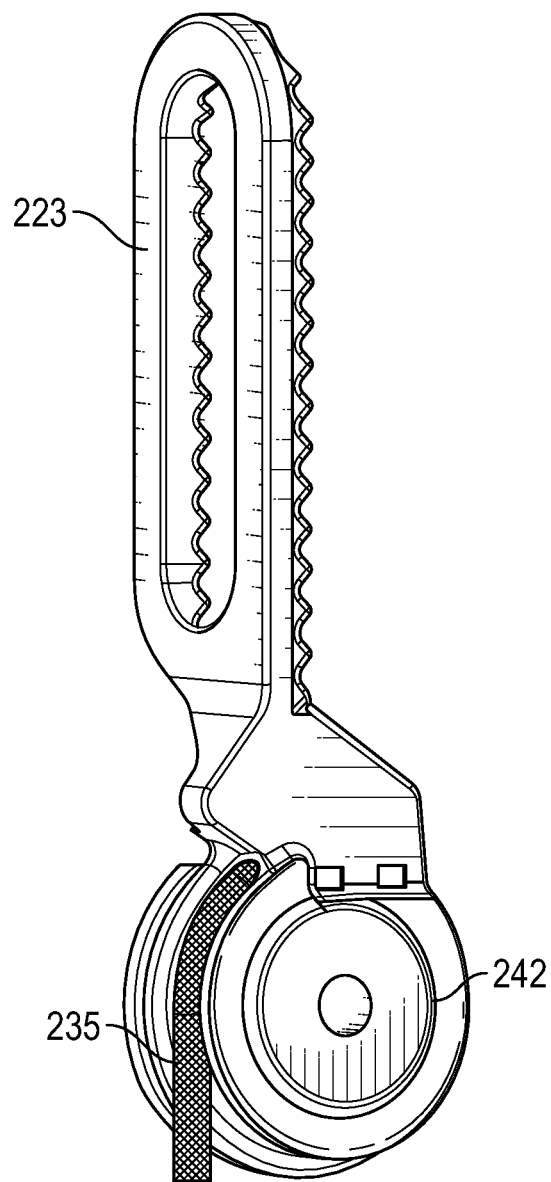
FIG. 23 illustrates a view of an embodiment of another end effector assembly in accordance with aspects of this disclosure.

The second end effector 223 may be formed as a single component with a corresponding distal pulley 242 (as shown in FIG. 23). In some embodiments, both the second end effector 223 and the distal pulley 242 can be formed at least in part of a conductive material, such as a metal. Thus, the second end effector 223 and the corresponding distal pulley may be electrically coupled to one another.

Due to the electrical insulation between at least the first end effector 221 and the distal pulley 240, one or more of the distal clevis 205, the proximal clevis 210, the distal pulleys 240, the distal axle 241, the proximal pulleys 245, the proximal axle 245, the proximal redirect pulleys 250, proximal redirect axle 251, the first drive cable 260, and the second drive cable 265 may be formed of a metal, such as, for example, tungsten, stainless steel, etc. The use of metal for one or more of the above-listed components may improve the durability of the bipolar medical instrument 200 as compared with the use of less wear-resistant materials. The use of metal can also increase the strength of the distal end of the bipolar medical instrument 200 without a corresponding increase in the overall diameter of the bipolar medical instrument 200.

Figure 22A:
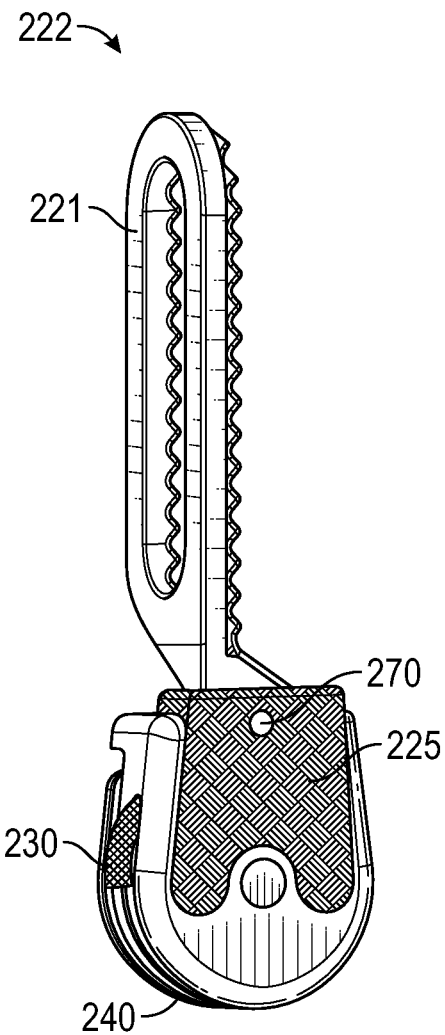
FIGS. 22A and 22B illustrate a plurality of views of an embodiment of an end effector assembly in accordance with aspects of this disclosure.
Figure 22B:
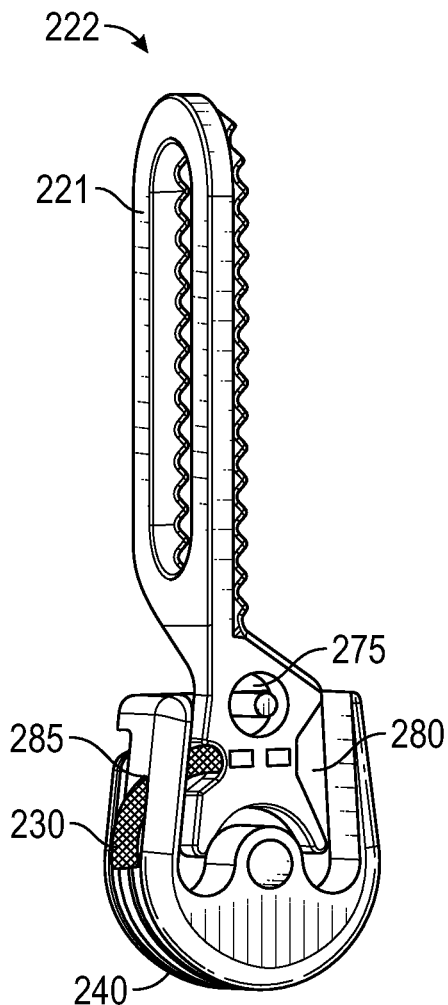

FIGS. 22A and 22B illustrate a plurality of views of an embodiment of an end effector assembly in accordance with aspects of this disclosure. Specifically, FIGS. 22A and 22B provide a more detailed view of an end effector assembly 222 including the first end effector 221, the insulating member 225, and the distal pulley 240 of FIGS. 21A-21D. FIG. 22A illustrates the first end effector 221 when coupled to the distal pulley 240 via the insulating member 225 while FIG. 22A provides an illustration with the insulating member 225 absent to show the relative positions or arrangement of the first end effector 221 and the distal pulley 240 with respect to each other.

The insulating member 225 may couple the first end effector 221 to the distal pulley 240. In some embodiments, the insulating member 225 may be coupled to each of the distal pulley 240 and the first end effector 221 via a mechanical interlock including a pin 270 formed between the first end effector 221 and the distal pulley 240. The pin 270 may be formed in the first distal pulley 240 and may be received in a first opening 275 formed in the first end effector 221. The pin 270 may extend from a surface of the first distal pulley 240 and into the first opening 275. A second opening or pocket 280 may be formed between the first end effector 221 and the distal pulley 240. The insulating member 225 may be shaped to fill each of the first opening 275 and the second opening 280 to electrically insulate the first end effector 221 from the distal pulley 240. The insulating member 225 may further mechanically couple the first end effector 221 to the distal pulley 240 such that forces applied to the distal pulley 240 via the first drive cable 260 are transmitted to the first end effector 221. Additionally, the first electrical cable 230 may run through a third opening 285 in the distal pulley 240 to be electrically connected to the first end effector 221. The first electrical cable 230 may be electrically insulated from the distal pulley 240.

One advantage to the mechanical interlock of FIGS. 22A and 22B including the pin 270 is that it serves as a safety feature that prevents the first end effector 221 from being inadvertently left behind as the bipolar medical instrument 200 is removed from the patient in the event that there is a connection failure of the insulating member 225 (e.g. resulting from damage to the insulating member 225). In some circumstances, if one or more of the end effectors 221, 223 are subjected to higher forces than under normal use, the insulating member 225 may break under the increased stress. If the insulating member 225 is broken while the bipolar medical instrument 200 is inside a patient's anatomy, the first opening 275 of the first end effector 221 will advantageously remain engaged with the pin 270 of the distal pulley 240. Thus, as the bipolar medical instrument 200 is removed from the patient, the pin 275 may hold the proximal portion of the first end effector 221 within the distal clevis 205, such that the first end effector 221 can be removed from the patient along with the bipolar medical instrument 200.

While FIGS. 22A and 22B illustrate a first end effector assembly including the first end effector 221 coupled to the distal pulley 240, FIG. 23 illustrates a second end effector assembly including the second end effector 223 coupled to the distal pulley 242. In this embodiment, the second end effector 223 is formed as a single component with the distal pulley 242. The second end effector 223 is electrically connected to the second electrical cable 235. Since the second end effector 223 is not electrically insulated from the distal pulley 242, the distal pulley 242 and the distal axle 241 may all be electrically connected to the second electrical cable 235. Since the distal axle 241 may be electrically connected to the wrist 201, the wrist 201 may also be electrically connected to the second electrical cable 235. In contrast, as the first end effector 221 is electrically insulated from the distal pulley 240 via the insulating member 225, the first end effector 221 can be effectively electrically insulated from the wrist 201 and other electrically conductive components of the bipolar medical instrument 200.

Although not illustrated, in some embodiments, the second end effector 223 may be static such that the second end effector 223 is not configured to move with respect to the distal clevis 205. The first end effector 221 may be configured to move relative to the second end effector 223 in a manner similar to the embodiment of FIGS. 21A-21D. The use of a static second end effector 223 may simplify the cable path design by removing the requirement for one of the DOF of movement and may also allow for a more compact design of the wrist 201 (e.g., by eliminating the need for a corresponding distal pulley mechanically coupled to the second end effector 223).

In another embodiment, the bipolar medical instrument 200 may not include the second electrical cable 235 and may instead provide a voltage potential to the second end effector 223 via an electrical path formed by the wrist 201 and/or the distal axle 241. For example, the second end effector 223 may be electrically coupled to the corresponding distal pulley, which in turn, may be electrically coupled to the wrist 201. Thus, the wrist 201 may be configured to provide an electric current to the second end effector 223. In this embodiment, the overall size of the bipolar medical instrument may be reduced by removing the spatial and cable routing requirements for the second electrical cable 235.

Figure 24A:
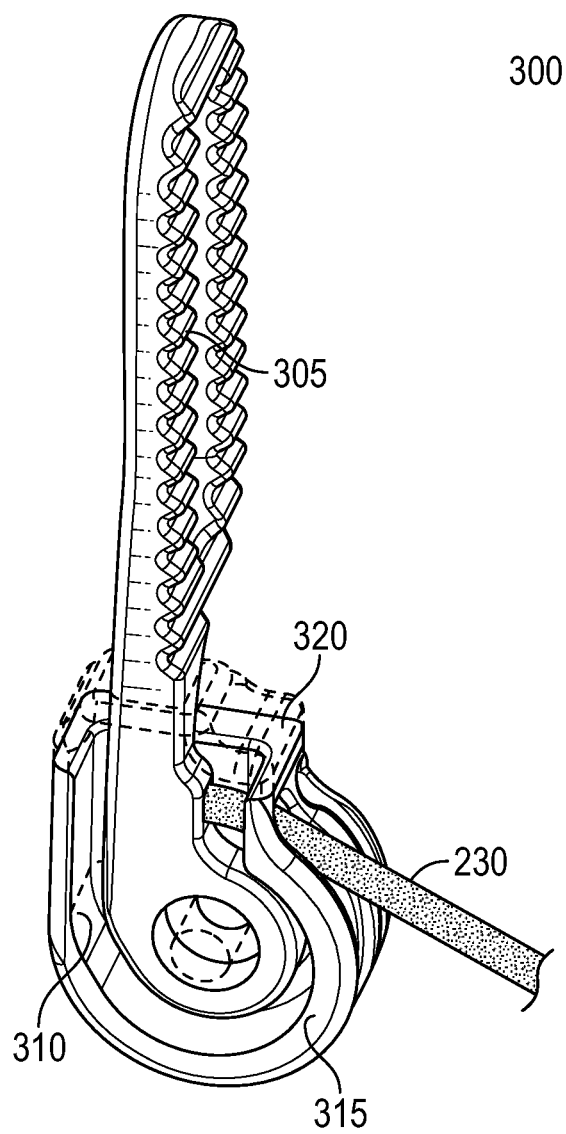
FIGS. 24A-24C illustrate plurality of views of another embodiment of an end effector and distal pulley assembly in accordance with aspects of this disclosure.
Figure 24B:
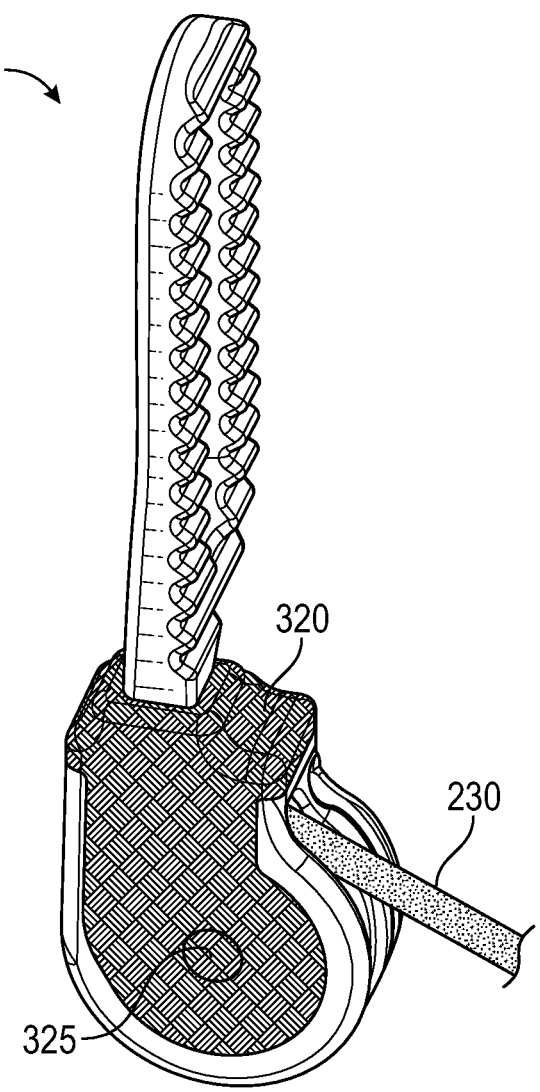
Figure 24C:
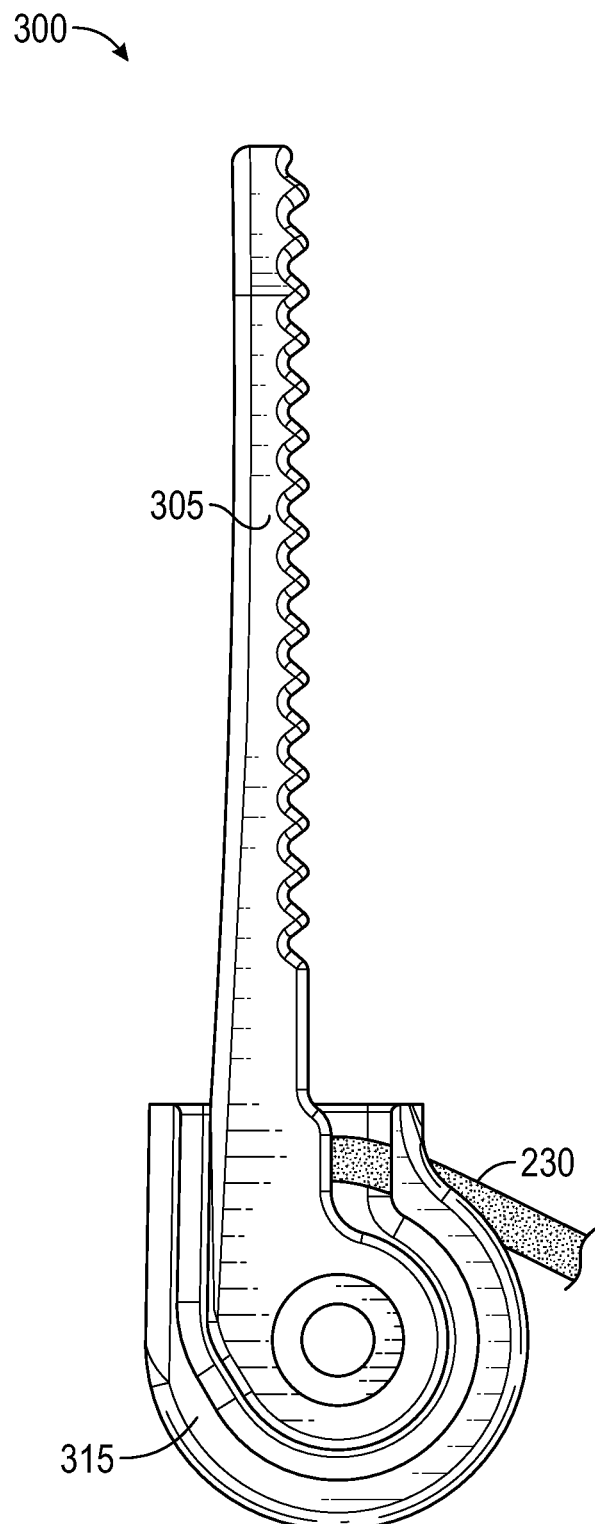

FIGS. 24A-24C illustrate a plurality of views of another embodiment of an end effector and distal pulley assembly in accordance with aspects of this disclosure. For example, the end effector assembly 300 illustrated in FIGS. 24A-24C may be used in place of the first end effector 221 and distal pulley 240 of FIGS. 21A-21D, or any other end effector and distal pulley assembly described herein.

The end effector assembly 300 includes an end effector 305, a distal pulley 315, and an insulating member 320. In particular, FIG. 24A illustrates the end effector assembly 300 with the insulating member 320 illustrated as transparent to show the opening or pocket 310 formed between the end effector 305 and the distal pulley 315. An electrical cable 230 may also be electrically connected to the end effector 305. FIG. 24B illustrates the end effector assembly 300 with the insulating member 320 coupled between the end effector 305 and the distal pulley 315. FIG. 24C provides an illustration without the insulating member 320 to show the relative positions of the end effector 305 and the distal pulley 315.

As shown in FIGS. 24A-24C, the end effector 305 is separate from the distal pulley 315 via the opening 310. The end effector 305 and insulating member 320 may form a channel 325 into which a distal axle (e.g., the distal axle 241 of FIG. 21B) can be inserted. The end effector 305 may form a ring at the proximal end which is concentric with the channel 325, and thus, with the distal axle when assembled to form a bipolar medical instrument. The insulating member 320 may fill the opening 310 to surround the ring at the proximal end of the end effector 305 and electrically insulate the end effector 305 from the distal pulley 315. In comparison to the embodiment of FIGS. 22A and 22B, the insulating member 320 of the embodiment of FIG. 24A-24C may occupy a larger portion of the face formed at the proximal end the end effector assembly 300 formed by the insulating member 320 and distal pulley 310. In some embodiments, the insulating member 320 may occupy about 70% or more of the face formed at the proximal end the end effector assembly 300.

B. Bipolar Medical Instruments Including Dual Isolated Grips.

Figure 25:
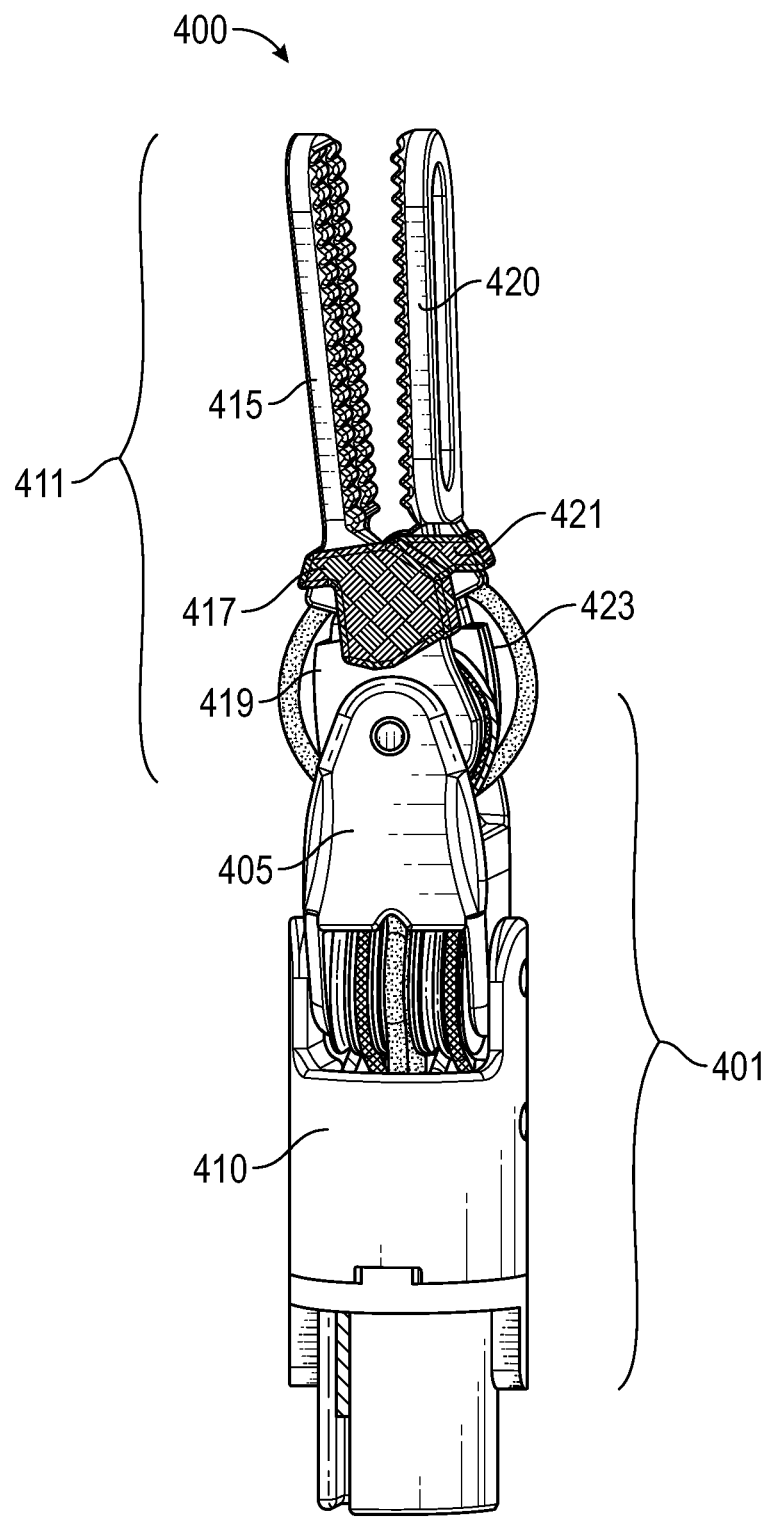
FIG. 25 illustrates another embodiment of a bipolar medical instrument in accordance with aspects of this disclosure.

FIG. 25 illustrates an embodiment of a bipolar medical instrument including dual isolated grips in accordance with aspects of this disclosure. Specifically, FIG. 25 illustrates a bipolar medical instrument 400 with a pair of end effectors 415 and 420. FIGS. 26A-26D illustrate a plurality of views of the end effector and distal pulley assembly of the instrument in FIG. 25 in accordance with aspects of this disclosure. In particular, FIGS. 26A-26D illustrate side views of: a first end effector assembly 411, the first end effector assembly 411 with the insulating member 417 absent, a cross-sectional view of the first end effector assembly 411, and a perspective review of the first end effector assembly 411 with the insulating member 417 absent, respectively.

Figures 26A, 26B:
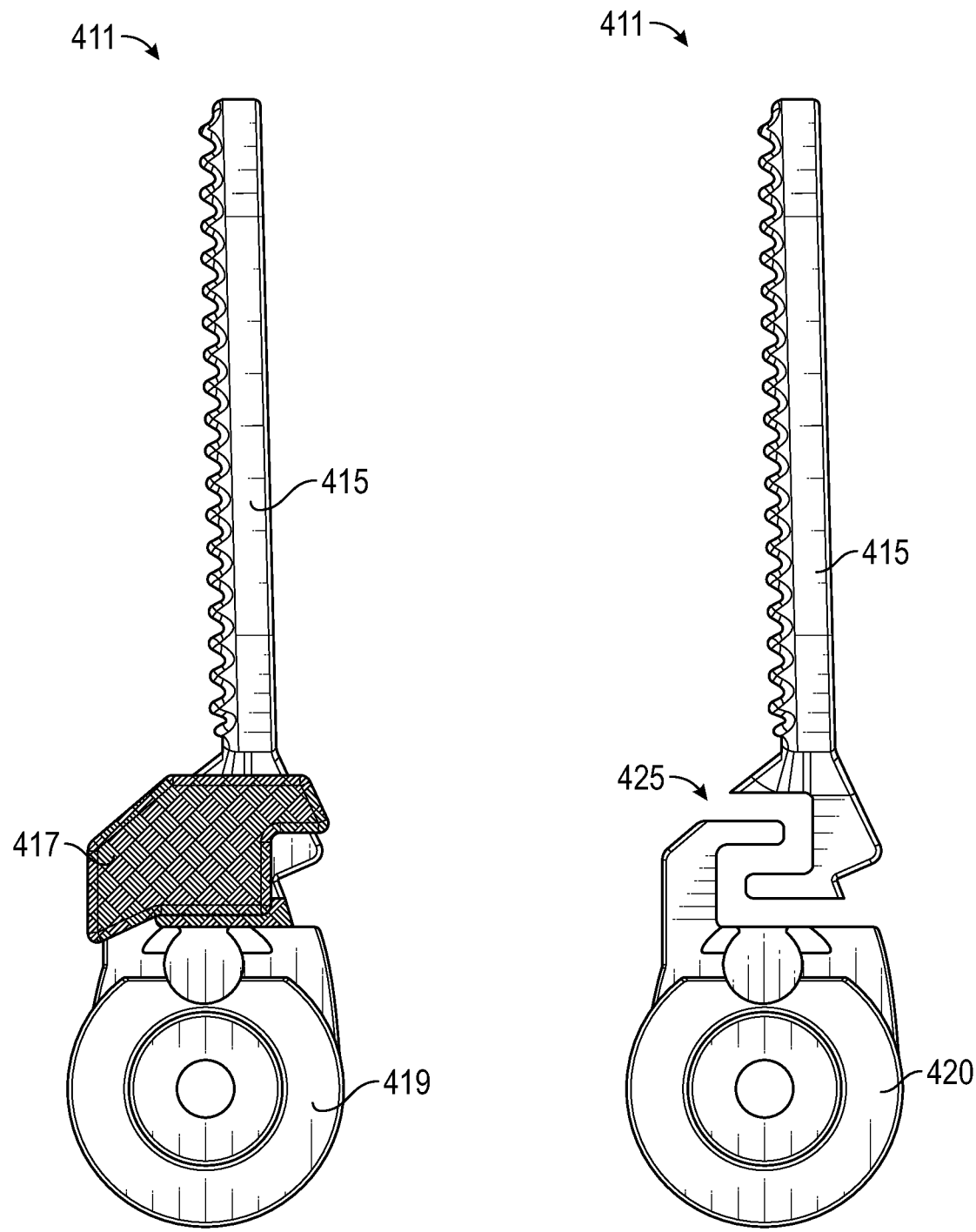

Referring to FIG. 25, the bipolar medical instrument 400 includes a wrist 401 including a distal clevis 405 and a proximal clevis 410, a first end effector 415, a first insulating member 417, and a first distal pulley 419, a second end effector 420, a second insulating member 421, and a second distal pulley 423. The first end effector 415, the first insulating member 417, and the first distal pulley 419 together form a first end effector assembly 411, which is illustrated in FIGS. 26A-26C. Certain components of the bipolar medical instrument 400 are similar to those of the bipolar medical instrument 200 illustrated in FIGS. 21A-21D, and thus, may function in a similar fashion to the previous description thereof.

In the embodiment of FIG. 25, each of the first and second end effectors 415 and 420 is electrically insulated from the wrist 401 by the first and second insulating members 417 and 421, respectively. Thus, each of the first and second end effectors 415 and 420 may be electrically connected to a separate electrical cable such that a voltage difference can be applied to the first and second end effectors 415 and 420.

Each of the first and second end effectors 415 and 420 may have a substantially similar construction, and thus the first end effector assembly 411 will be described in connection with FIGS. 26A-26C. The first end effector 415 may be separated from the first distal pulley 419 by the first insulating member 417. A proximal portion of the first end effector 415 may overlap a distal portion of the first distal pulley 419 along a longitudinal axis and transverse axis of the first end effector 415 to form a tortuous void 425 between the first end effector 415 and the first distal pulley 419. The first insulating member 417 may be shaped to fill the tortuous void 425, thereby mechanically coupling the first distal pulley 419 to the first end effector 415 such that forces applied to the first distal pulley 419 are transmitted to the first end effector 415.

As shown in FIG. 26B, the tortuous void 425 may be S-shaped when viewed from the side. Additionally, the tortuous void 425 may include channels formed in each of the protrusions forming the S-shape on the distal end of the first distal pulley 419 and the proximal end of the first end effector 415 as shown in FIG. 26D. The first end effector 415 may further include a receptacle 425 for an electrical cable to receive a voltage from a generator via the electrical cable. The insulating member 417, which is formed through the tortuous void, can be applied to any of the embodiments described herein.

Figure 27A:
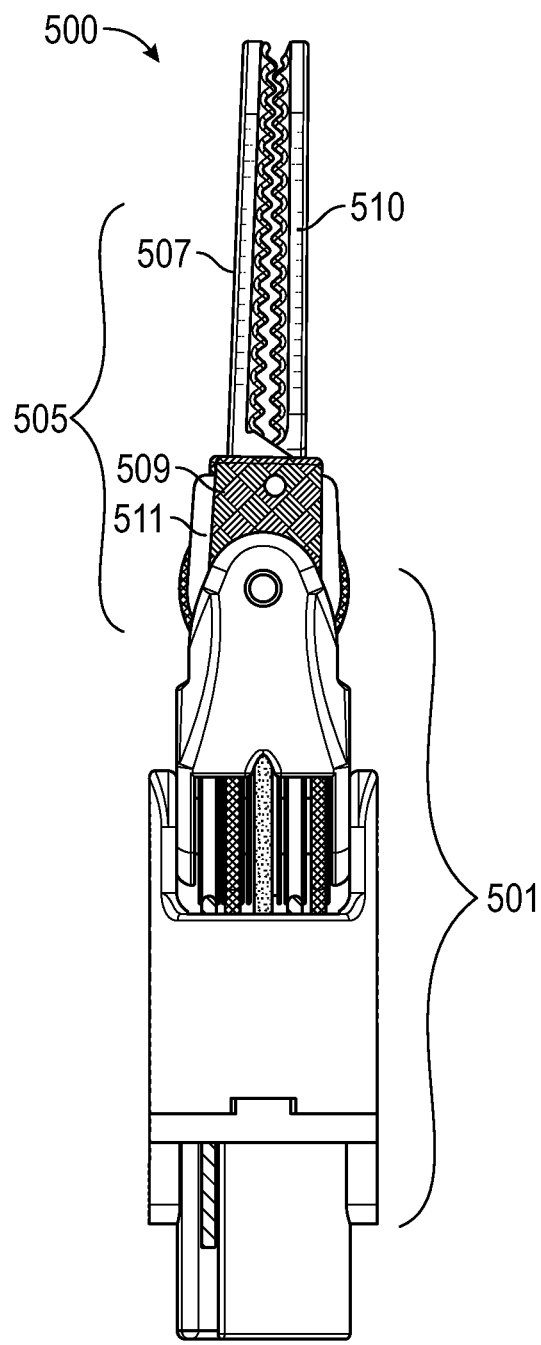
FIGS. 27A and 27B illustrate yet another embodiment of a bipolar medical instrument in accordance with aspects of this disclosure.
Figure 27B:
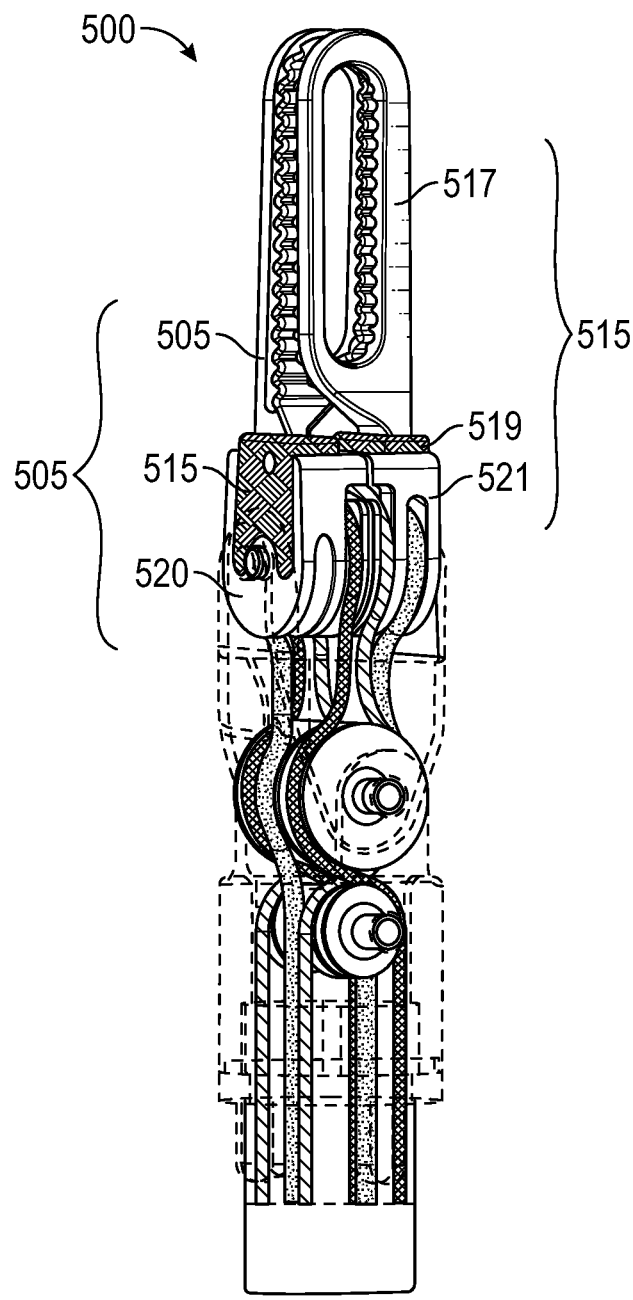

FIGS. 27A and 27B illustrate yet another embodiment of a bipolar medical instrument including dual isolated grips in accordance with aspects of this disclosure. The bipolar medical instrument 500 may include: a wrist 501; a first end effector assembly 505 including a first end effector 507, a first insulating member 509, and a first distal pulley 511; and a second end effector assembly 515 including a second end effector 517, a second insulating member 519, and a second distal pulley 521.

Similar to the embodiment of FIG. 25, in the bipolar medical instrument 500 of FIGS. 27A and 27B, each of a first end effector 507 and a second end effector 517 may be electrically insulated from the wrist 501. Further, the design of each of the first end effector assembly 505 and the second end effector assembly 515 is similar to that of the end effector assembly 222 of FIGS. 22A and 22B.

In addition, the bipolar medical instrument 500 of the embodiment of FIGS. 27A and 27B may employ pulley sharing where each of the first cable segments shares one of the proximal pulleys and one of the proximal redirect pulleys with one of the second cable segments. Further, the electrical cable in the embodiment of embodiment FIGS. 27A and 27B may be routed through a center of the wrist such that only one electrical cable is present in the wrist. In other embodiments, a pair of electrical cables can be present in the wrist.

The embodiments in FIGS. 21A-24C (e.g., single isolated grip embodiments) and FIGS. 25-27B (e.g., dual isolated grip embodiments) are particularly useful for insulation when the distal pulleys that are coupled to the grips are formed of a conductive material such as metal. As an alternative to embodiments wherein the distal pulleys are formed of metal, it is possible for at least one distal pulley to be formed of a non-conductive material of a high dielectric strength. In some embodiments, the one or more non-conductive distal pulleys can then be used with or without the insulative skirts. Such embodiments are described below in FIGS. 28-29B.

C. Bipolar Medical Instruments Including One or More Non-Conductive Pulleys.

Figure 28:
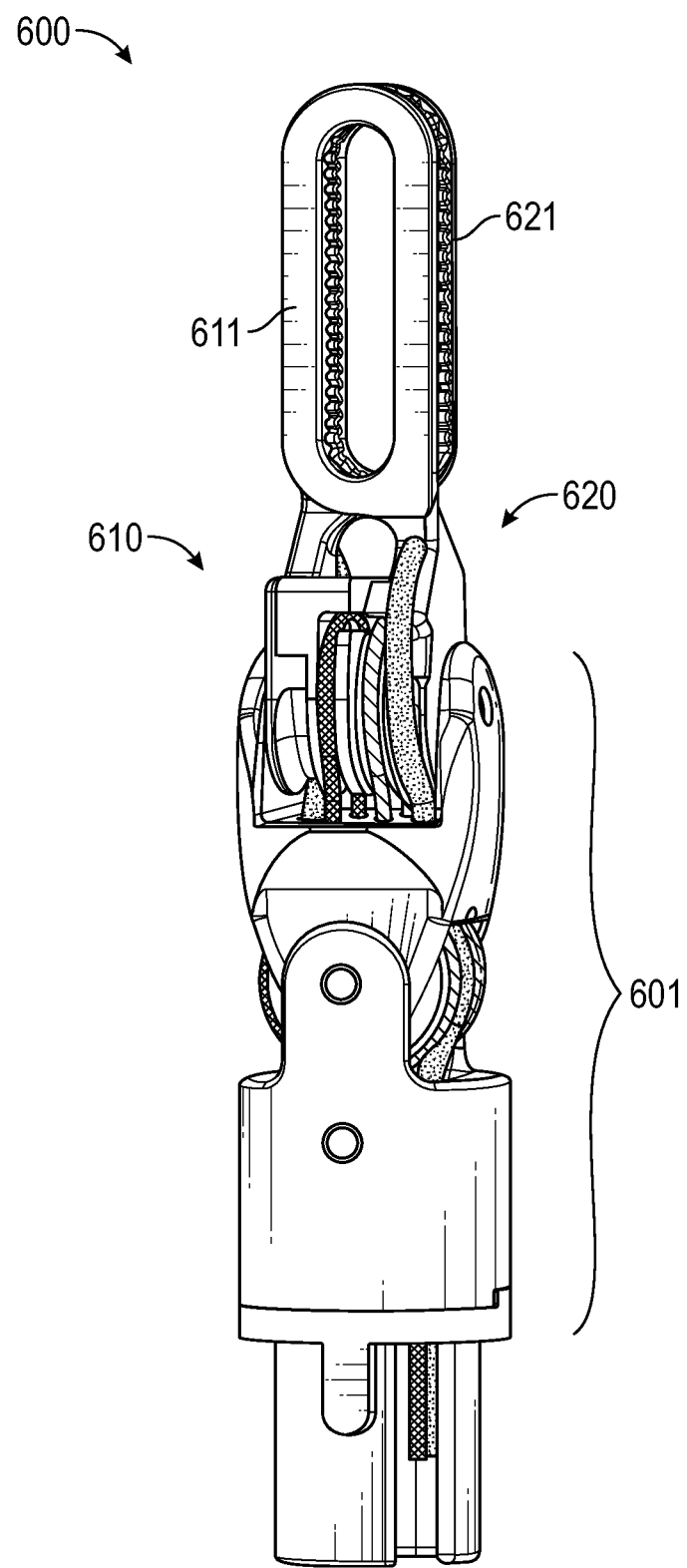
FIG. 28 illustrates yet another embodiment of a bipolar medical instrument in accordance with aspects of this disclosure.

FIG. 28 illustrates yet another embodiment of a bipolar medical instrument in accordance with aspects of this disclosure. Specifically, FIG. 28 illustrates a bipolar medical instrument 600 having a wrist 601, a first end effector assembly 610 including a first end effector 611, and a second end effector assembly 620 including a second end effector 621. In the embodiment of FIG. 28, the first end effector 611 may be electrically insulated from portions of the wrist 601 via a distal pulley that is formed of a non-conductive material, while the second end effector assembly 620 may not be electrically insulated from the wrist 601. In particular, in some embodiments, the second end effector assembly 620 may be electrically connected to the wrist 601 and may receive a voltage potential via the wrist 601 forming a portion of the electrical path.

Figure 29A:
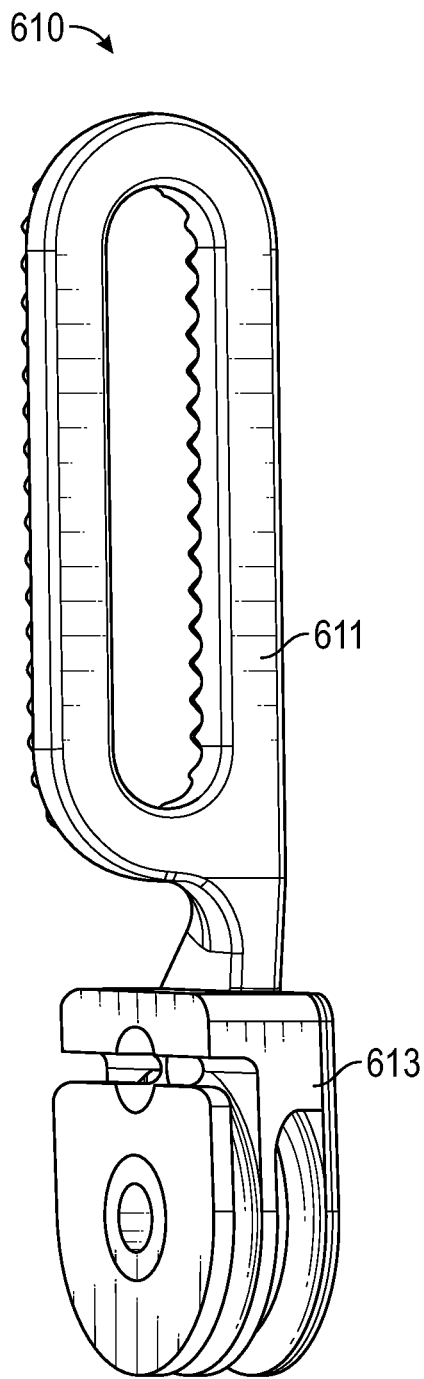
FIG. 29A illustrates an embodiment of a first end effector in accordance with aspects of this disclosure.
Figure 29B:
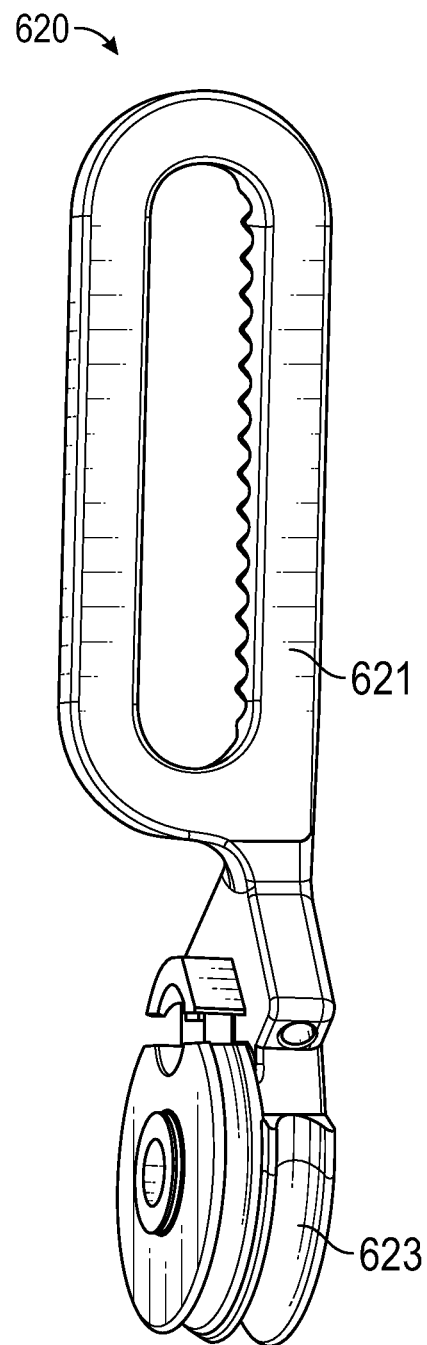
FIG. 29B illustrates an embodiment of a second end effector in accordance with aspects of this disclosure.

FIG. 29A illustrates an embodiment of a first end effector assembly 610 in accordance with aspects of this disclosure and FIG. 29B illustrates an embodiment of a second end effector assembly 620 in accordance with aspects of this disclosure. As shown in FIG. 29A, the first end effector assembly 610 includes the first end effector 611 and a first distal pulley 613. In more detail, the first distal pulley 613 may be formed of an electrically insulating material with a high dielectric strength (e.g., urethane, peek, ultem, epoxy resin, ceramic, one or more plastics, etc.). Since the distal pulley 613 is formed of an electrically insulating material, the first end effector 611 is electrically insulated from portions of the wrist 601. In other embodiments, the first end effector assembly 610 further includes an insulating member (not illustrated) coupled between the first end effector 611 and the distal pulley 613, where each of the insulating member and the distal pulley 613 is formed of an electrically insulating material.

With reference to FIG. 29B, the second end effector assembly 620 may be similar to the second end effector 223 of FIG. 23. For example, the second end effector 621 and the second distal pulley 623 may be formed as a single component or may be formed of two separate components with are electrically connected to each other.

D. Example Method for Actuating an End Effector in Multiple Degrees of Movement.

Figure 30:
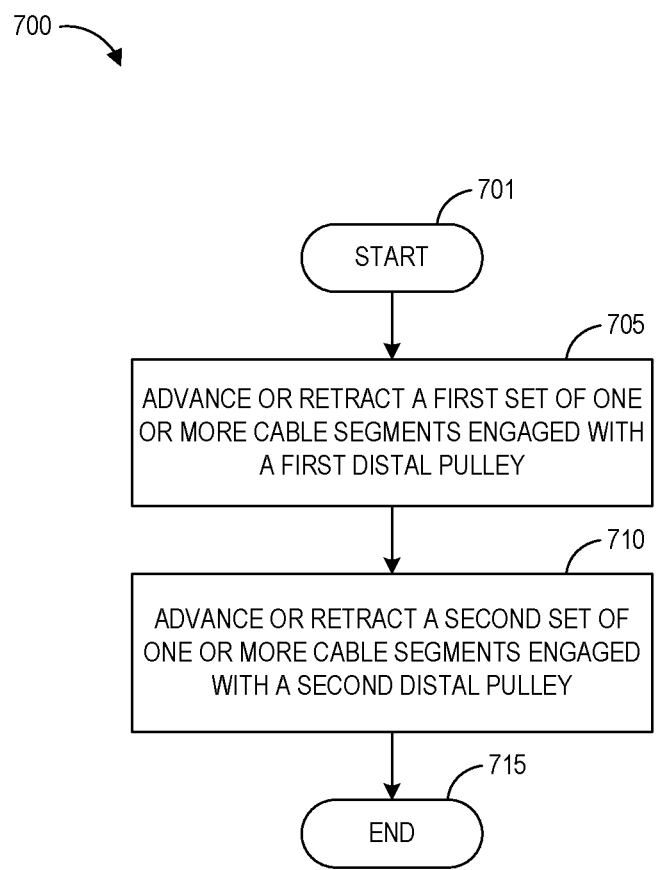
FIG. 30 is a flowchart illustrating an example method operable by a robotic system, or component(s) thereof, for actuating an end effector in multiple degrees of movement in accordance with aspects of this disclosure.

FIG. 30 is a flowchart illustrating an example method operable by a robotic system, or component(s) thereof, for actuating an end effector in multiple degrees of movement in accordance with aspects of this disclosure. For example, the steps of method 700 illustrated in FIG. 30 may be performed by processor(s) and/or other component(s) of a medical robotic system (e.g., robotically-enabled system 10) or associated system(s). For convenience, the method 700 is described as performed by the "system" in connection with the description of the method 700.

The method 700 begins at block 701. At block 705, the system may advance or retract a first set of one or more cable segments engaged with a first distal pulley. The instrument may be implemented as shown in FIGS. 21A-21D, FIG. 25, FIG. 27, or FIG. 28, and include the first distal pulley coupled to a first end effector and configured to actuate the first end effector in a first degree of movement. The first end effector may be electrically insulated from the first distal pulley via a first insulating member.

At block 710, the system may advance or retract a second set of one or more cable segments engaged with a second distal pulley. The second distal pulley may be coupled to a second end effector and configured to actuate the second end effector in a second degree of movement. In certain implementations, the method 700 may further include the system advancing or retracting the first set of one or more cable segments and the second set of one or more cable segments to rotate the first end effector and the second end effector in a third degree of movement. The first set of one or more cable segments and the second set of one or more cable segments may be engaged with a first proximal pulley and a second proximal pulley, respectively. In some embodiments, the steps in blocks 705 and 710 can be performed sequentially, while in other embodiments, the steps in blocks 705 and 710 can be performed in concert. The method 700 ends at block 715.

E. Example Method for Manufacturing a Bipolar Medical Instrument.

Figure 31:
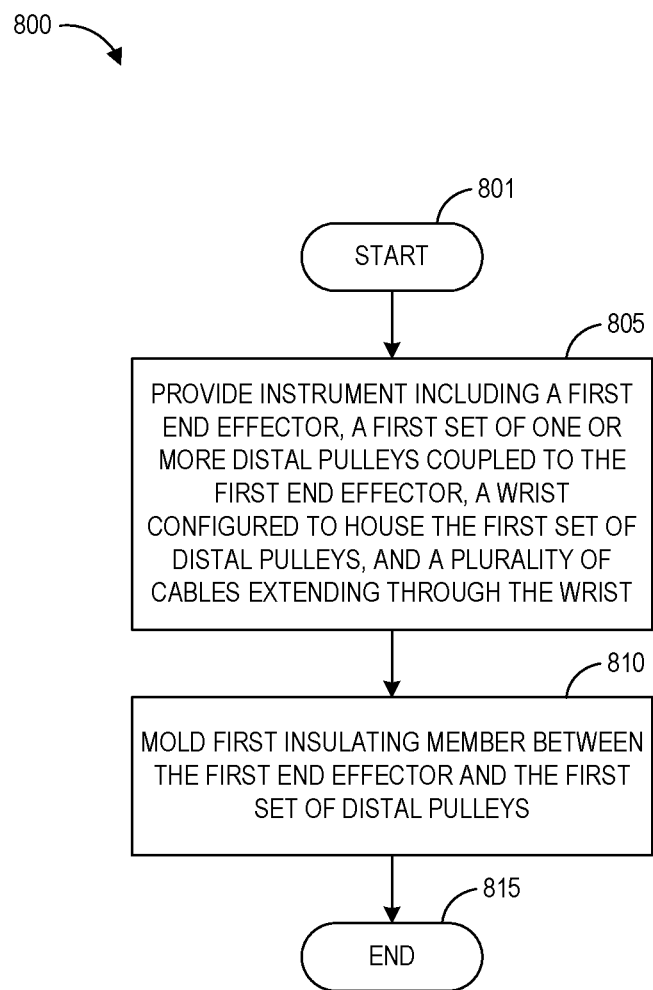
FIG. 31 is a flowchart illustrating an example method for manufacturing a bipolar medical instrument in accordance with aspects of this disclosure.

FIG. 31 is a flowchart illustrating an example method for manufacturing a bipolar medical instrument in accordance with aspects of this disclosure. The bipolar medical instrument manufactured according to the method 800 may be implemented as shown in FIGS. 21A-21D, FIG. 25, FIG. 27, or FIG. 28.

The method 800 begins at block 801. At block 805, the method 800 includes providing an instrument including: a first end effector and a first set of one or more distal pulleys.

At block 810, the method 800 includes molding a first insulating member between the first end effector and the first set of distal pulleys. The first insulating member electrically isolates the first end effector from the first set of one or more distal pulleys. In certain implementations, molding the first insulating member includes insert molding. The method 800 ends at block 815.

In some embodiments, the assembly including the first end effector, the first set of distal pulleys and the first insulating member can then be coupled to an instrument wrist. In other embodiments, the first set of distal pulleys can already be coupled to an instrument wrist before insert molding the first insulating member.

3. Implementing Systems and Terminology

Implementations disclosed herein provide systems, methods and apparatus for an articulating medical instrument which may include a bipolar end effector.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions associated with the articulating medical instrument described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical instrument, comprising:
   a first end effector;
   a first set of one or more distal pulleys coupled to the first end effector and configured to form an opening between the first end effector and the first set of one or more distal pulleys;
   a wrist configured to house the first set of distal pulleys;
   a plurality of cables extending through the wrist; and
   a first insulating member formed in the opening between the first end effector and the first set of one or more distal pulleys, the first insulating member mechanically coupling the first end effector to the first set of one or more distal pulleys.

2. The instrument of claim 1, wherein the first end effector and the first set of one or more distal pulleys are formed of metal.

3. The instrument of claim 1, further comprising:
   a second end effector; and
   a second set of one or more distal pulleys coupled to the second end effector.

4. The instrument of claim 3, wherein the second end effector and the second set of one or more distal pulleys are electrically coupled.

5. The instrument of claim 3, wherein the wrist is configured to provide an electric current to the second end effector.

6. The instrument of claim 3, further comprising a second insulating member formed between the second end effector and the second set of distal pulleys.

7. The instrument of claim 3, wherein:
the first end effector comprises a first jaw and the second end effector comprises a second jaw;
the first jaw and the second jaw are configured to form a bipolar grasping device.

8. The instrument of claim 3, wherein:
the first end effector and the first set of distal pulleys are electrically decoupled from one another, and
the second end effector and the second set of distal pulleys are electrically coupled to one another.

9. The instrument of claim 3, wherein an axle extends through the first set of distal pulleys and the second set of distal pulleys.

10. The instrument of claim 9, further comprising a set of one or more proximal pulleys.

11. The instrument of claim 9, further comprising:
a set of one or more proximal pulleys; and
a set of one or more proximal redirect pulleys.

12. The instrument of claim 1, further comprising a second end effector, wherein:
the second end effector is static, and
the first end effector is configured to move relative to the second end effector.

13. The instrument of claim 1, wherein the first end effector and the first set of one or more distal pulleys are coupled together via a mechanical connection formed by a pin.

14. The instrument of claim 13, wherein the pin is formed in the first set of one or more distal pulleys and is received in an opening formed in the first end effector.

15. The instrument of claim 1, further comprising:
an axle extending through the first set of distal pulleys, wherein first end effector forms a ring concentric with the axle.

16. The instrument of claim 15, wherein the first insulating member surrounds at least a portion of the ring.

17. The instrument of claim 1, wherein:
the first end effector comprises a longitudinal axis and a transverse axis perpendicular to the longitudinal axis;
a proximal portion of the first end effector overlaps a distal portion of the first set of distal pulleys along the longitudinal axis and transverse axis to form a tortuous void between the first end effector and the first set of distal pulleys; and
the first insulating member fills the tortuous void.

18. The instrument of claim 17, wherein the tortuous void is S-shaped.

19. The instrument of claim 1, wherein the first insulating member and the first set of distal pulleys are formed of an electrically insulating material.

* * * * *